Figure 1:
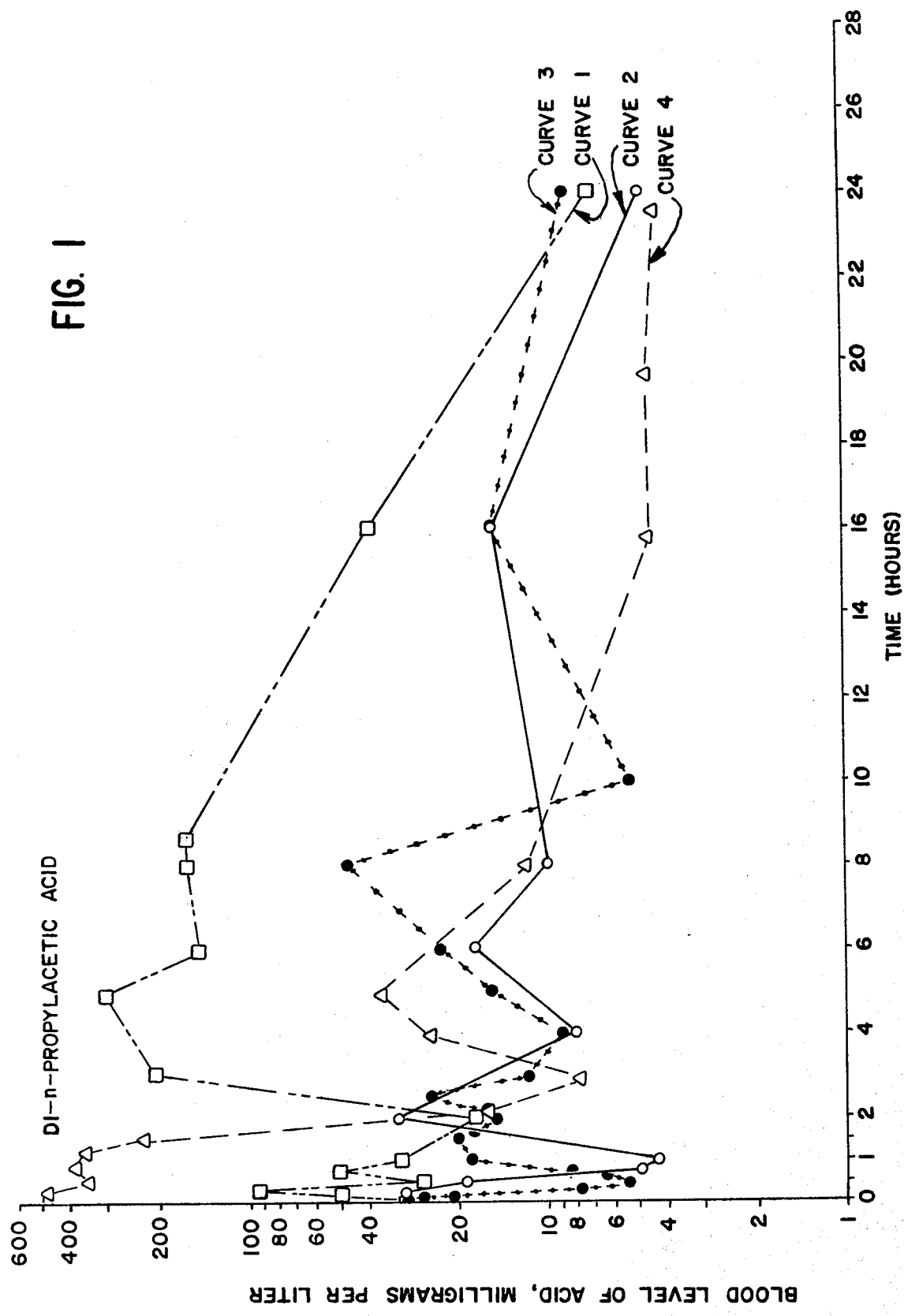

United States Patent [19]

Chignac et al.

[11] 4,423,071

[45] Dec. 27, 1983

[54] POLYOL DERIVATIVES, PROCESSES FOR PREPARING THE SAME AND THEIR USES IN THERAPEUTICS

[75] Inventors: Michel Chignac, Sisteron; Claude Grain, Volonne; Fernand Jammot, Sisteron; Charles Pigerol, Saint-Ouen; Pierre Eymard, Fontaine; Bernard Ferrandes, Claix, all of France

[73] Assignee: Sanofi, Courbevoie, France

[21] Appl. No.: 126,191

[22] Filed: Mar. 3, 1980

[30] Foreign Application Priority Data

Mar. 6, 1979 [GB] United Kingdom ................ 7907932

[51] Int. Cl.³ ............................................. A61K 31/22
[52] U.S. Cl. ................................... 424/311; 549/453; 549/454; 549/561; 560/121; 560/126; 560/129; 560/179; 560/187; 560/188; 560/189; 560/201; 560/263; 424/278
[58] Field of Search ............... 560/121, 126, 129, 187, 560/188, 201, 263; 424/311; 260/340.9, 348.59

[56] References Cited

U.S. PATENT DOCUMENTS

| | | | |
|---|---|---|---|
| 2,010,154 | 8/1935 | Hubacher | 560/126 |
| 2,348,710 | 5/1944 | Caryl | 560/126 |
| 2,362,326 | 11/1944 | Thurston et al. | 560/126 |
| 2,446,505 | 8/1948 | Arenson | 424/311 |
| 2,474,796 | 6/1949 | Van Campen, Jr. | 560/126 |
| 2,627,489 | 2/1953 | Drake | 424/311 |
| 2,807,638 | 9/1957 | Morris et al. | 560/1 |
| 2,920,056 | 1/1960 | Banes et al. | 560/223 |
| 2,962,419 | 11/1960 | Minich | 560/223 |
| 3,178,454 | 4/1965 | Kloos et al. | 260/348.59 |
| 3,282,971 | 11/1966 | Metro et al. | 560/223 |
| 3,972,914 | 8/1976 | Vanlerberghe et al. | 560/223 |
| 4,178,261 | 12/1979 | Dhein et al. | 560/223 |
| 4,199,599 | 4/1980 | Klein | 560/223 |

FOREIGN PATENT DOCUMENTS

| | | | |
|---|---|---|---|
| 18342 | 10/1980 | European Pat. Off. | 424/311 |
| 596326 | 7/1959 | Italy | 260/340.9 R |

OTHER PUBLICATIONS

Chem. Abstracts, 8th Collective Index, (1967-1971), p. 24626e.
Chem. Abstracts, 9th Collective Index, (1972-1976), p. 31236cs.
Chem. Abstracts 52: P2062a.
Meijer et al., Proceedings Symposium Nottingham University, Sep. 23-24, 1975.

*Primary Examiner*—Ethel G. Love
*Attorney, Agent, or Firm*—Mason, Kolehmainen, Rathburn & Wyss

[57] ABSTRACT

Mono-, di-, tri- and tetra-esters derived from an acid of the general formula:

$$R-OH$$

in which R represents an acyl radical of the general formula:

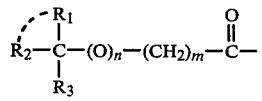

in which n represents 0 or 1, m represents 0, 1, 2, 3 or 4, $R_1$ and $R_2$ each represent a straight- or branched-chain alkyl radical having from 1 to 5 carbon atoms, $R_3$ represents hydrogen or a straight- or branched-chain alkyl radical having from 1 to 5 carbon atoms, the sum of the carbon atoms in $R_1$ and $R_2$ being from 4 to 10 when $R_3$ represents hydrogen and the sum of the carbon atoms in $R_1$, $R_2$ and $R_3$ being from 6 to 15 when $R_3$ is different from hydrogen, or $R_1$ and $R_2$ when they are taken together represent a tetramethylene, pentamethylene or hexamethylene radical and $R_3$ represents a straight-chain alkyl radical and an alcohol selected from the group consisting of glycerol, 2,3-epoxy-propanol, 1,2-propanediol, 1,3-propanediol, 1,2-butanediol, 1,3-butanediol, 1,4-butanediol, 1,2,3-butanetriol, 1,2,4-butanetriol, 1,2,3,4-butanetetrol, 2-buten-1,4-diol, 2-butyn-1,4-diol, diethyleneglycol, a cyclohexanediol preferably 1,2-cyclohexanediol, thiodiglycol, diethanolamine, N-R-substituted-diethanolamine, trimethylolpropane, pentaerythritol and an alcohol of the general formula:

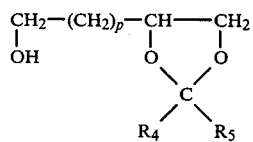  II in which p represents 0 or 1, R₄ represents methyl, R₅ represents methyl, ethyl, 2-methyl-butyl or R₄ and R₅, when they are taken together represent a pentamethylene radical, with the exception of glyceryl tri-(di-n-propylacetate).

These esters are useful in the treatment of central nervous system disorders and including, in particular, convulsive states and seizures, and disorders relating to the field of neuropsychiatry.

6 Claims, 11 Drawing Figures

POLYOL DERIVATIVES, PROCESSES FOR PREPARING THE SAME AND THEIR USES IN THERAPEUTICS

This invention relates to polyol derivatives having pharmacological activity to pharmaceutical and veterinary compositions containing them and to a process for preparing these derivatives and compositions.

The pharmacologically active compounds with which the present invention is concerned consist of the mono-, di-, tri- and tetra-esters derived from an acid of the general formula:

R—OH  I in which R represents an acyl radical of the general formula:

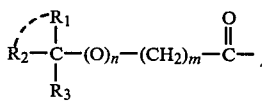

in which n represents 0 or 1, m represents 0, 1, 2, 3 or 4, $R_1$ and $R_2$ each represent a straight- or branched-chain alkyl radical having from 1 to 5 carbon atoms, $R_3$ represents hydrogen or a straight- or branched-chain alkyl radical having from 1 to 5 carbon atoms, the sum of the carbon atoms in $R_1$ and $R_2$ being from 4 to 10 when $R_3$ represents hydrogen and the sum of the carbon atoms in $R_1$, $R_2$ and $R_3$ being from 6 to 15 when $R_3$ is different from hydrogen, or $R_1$ and $R_2$ when they are taken together represent a tetramethylene, pentamethylene or hexamethylene radical and $R_3$ represents a straight-chain alkyl radical and an alcohol selected from the group consisting of glycerol, 2,3-epoxy-propanol, 1,2-propanediol, 1,3-propanediol, 1,2-butanediol, 1,3-butanediol, 1,4-butanediol, 1,2,3-butanetriol, 1,2,4-butanetriol, 1,2,3,4-butanetetrol, 2-buten-1,4-diol, 2-butyn-1,4-diol, diethyleneglycol, a cyclohexanediol preferably 1,2-cyclohexanediol, thiodiglycol, diethanolamine, N-R-substituted-diethanolamine, trimethylolpropane, pentaerythritol and alcohol of the general formula:

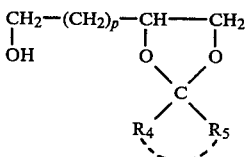

in which p represents 0 or 1, $R_4$ represents methyl, ethyl, 2-methyl-butyl or $R_4$ and $R_5$, when they are taken together represent a pentamethylene radical, with the exception of glyceryl tri(di-n-propylacetate).

One class of compounds falling within the scope of the compounds of the invention consists of the esters derived from an acid of general formula I above, and an alcohol selected from the group consisting of glycerol, 1,2-propanediol, 1,3-propanediol, 1-3,butanediol, 1,4-butanediol, 1,2,4-butanetriol, 2-buten-1,4-diol, 2-butyn-1,4-diol, diethyleneglycol, 1,2-cyclohexanediol, thiodiglycol, N-R-substituted-diethanolamine, trimethylolpropane, pentaerythritol or an alcohol of the general formula II above, with the exception of glyceryl tri-(di-n-propylacetate).

A pharmacologically preferred class of compounds of the invention are the esters derived from an acid of formula I above wherein n represents 0 or 1, m represents 0, 1, 2 or 3, $R_1$ and $R_2$ each represent ethyl, n-propyl or n-butyl, $R_3$ represents hydrogen, methyl or n-propyl or $R_1$ and $R_2$, when they are taken together, represent a pentamethylene radical and $R_3$ represents methyl, and an alcohol selected from the group consisting of glycerol, 1,2-propanediol, 1,3-propanediol, 1,3-butanediol, 1,4-butanediol, 1,2,4-butanetriol, 2-buten-1,4-diol, 2-butyn-1,4-diol, diethyleneglycol, thiodiglycol, 1,2-cyclohexanediol, N-R-substituted-diethanolamine, trimethylolpropane, pentaerythritol or an alcohol of the general formula II above, with the exception of glycerol tri-(di-n-propylacetate).

Amongst the aforesaid class of compounds of the invention, the preferred esters are those derived from di-n-propylacetic acid and an alcohol selected from glycerol, 1,2-propanediol and 1,3-propanediol.

Examples of compounds falling within the scope of the present invention are listed hereunder.

These compounds, which can be regarded as novel compounds constitute another object of the invention:

1-(Di-n-propylacetyl)-2,3-isopropylidene-glycerol
1-(Tri-n-propylacetyl)-2,3-isopropylidene-glycerol
1-(2-Ethylhexanoyl)-2,3-isopropylidene-glycerol
1-(1-Methyl-cyclohexylcarbonyl)-2,3-isopropylidene-glycerol
1-(2-Methyl-2-ethylhexanoyl)-2,3-isopropylidene-glycerol
1-(Di-n-propylacetyl)-3,4-isopropylidene-1,3,4-butanetriol
1-(Di-n-propylmethoxyacetyl)-2,3-isopropylidene-glycerol
1-(4-n-Propylheptanoyl)-2,3-isopropylidene-glycerol
1-(Di-n-propylacetyl)-2,3-cyclohexylidene-glycerol
Glyceryl 1-(di-n-propylacetate)
Glyceryl 1-(tri-n-propylacetate)
Glyceryl 1-(2-ethylhexanoate)
Glyceryl 1-(1-methyl-cyclohexylcarboxylate)
Glyceryl 1-(2-methyl-2-ethylhexanoate)
Glyceryl 2-(di-n-propylacetate)
Glyceryl 1,2-bis-(di-n-propylacetate)
Glyceryl 1,2-bis-(2-ethylhexanoate)
Glyceryl 1,2-bis-(1-methyl-cyclohexylcarboxylate)
Glyceryl 1,2-bis-(tri-n-propylacetate)
Glyceryl 1,2-bis-(2-methyl-2-ethylhexanoate)
2,3-Epoxy-propyl-di-n-propylacetate
Glyceryl 1,3-bis-(di-n-propylacetate)
Glyceryl 1-(di-n-propylacetate)-3-(1-methyl-cyclohexylcarboxylate)
Glyceryl 1-(di-n-propylacetate)-3-(2-methyl-2-ethylhexanoate)
Glyceryl 1-(di-n-propylacetate)-2-(1-methyl-cyclohexylcarboxylate)
Glyceryl 1,2,3-tri-(1-methyl-cyclohexylcarboxylate)
1,2-Propanediol bis-(di-n-propylacetate)
1,3-Propanediol bis-(di-n-propylacetate)
1,3-Butanediol bis-(di-n-propylacetate)
1,4-Butanediol bis-(di-n-propylacetate)
2-Buten-1,4-diol bis-(di-n-propylacetate) (cis isomer)
2-Butyn-1,4-diol bis-(di-n-propylacetate)
Diethyleneglycol bis-(di-n-propylacetate)
Thiodiglycol bis-(di-n-propylacetate)
Glyceryl 1-(di-n-propylacetate)-2,3-bis-(1-methyl-cyclohexylcarboxylate)
1,2-Cyclohexanediol bis-(di-n-propylacetate)

N-(di-n-propylacetyl)-diethanolamine bis-(di-n-propylacetate)
1,2,4-Butanetriol tri-(di-n-propylacetate)
1-(Di-n-propylacetoxy)-3,4-butanediol
1,3-Propanediol bis-(1-methyl-cyclohexylcarboxylate)
Glyceryl 1-(di-n-propylmethoxyacetate)
Glyceryl 1-(4-n-propylheptanoate)
Glyceryl 1-(5-n-propyloctanoate)
1,2-Propanediol bis-(1-methyl-cyclohexylcarboxylate)
Trimethylolpropane tri-(di-n-propylacetate)
Pentaerythritol tetra-(di-n-propylacetate)

As will be described further on, suitable mixtures of esters of the invention, which can be regarded as novel compounds, were found to be particularly useful.

Therefore, a further object of the invention relates to mixtures of esters of the invention, for instance mixtures of glyceryl 1,2-bis-(di-n-propylacetate)/glyceryl 1,3-bis-(di-n-propylacetate), mixtures of glyceryl 1,2-bis-(di-n-propylpropionate)/glyceryl 1,3-bis-(di-n-propylpropionate) and mixtures of glyceryl 1,2-bis-(di-n-propylmethoxyacetate)/glyceryl 1,3-bis-(di-n-propylmethoxyacetate).

Compounds of the invention possess isomeric centres and thus can be produced as optical isomers, position isomers or mixtures of these isomers. The mixtures of these isomers can be resolved, if desired, at appropriate stages by methods known to those skilled in the art to obtain the respective individual isomers.

It is understood that these isomers as well as mixtures thereof are included within the scope of the present invention.

In accordance with another aspect of the invention there is provided a pharmaceutical or veterinary composition comprising, as an essential active ingredient, at least one ester of the invention in association with a pharmaceutical carrier or excipient therefor.

A further object of the invention is to provide a process for preparing pharmaceutical or veterinary compositions whereby at least one ester of the invention is associated with an appropriate pharmaceutical carrier or excipient.

As will be described in greater detail further on, it has been found that the esters of the invention are endowed with bio-chemical and pharmacological properties likely to render them particularly useful in the treatment of pathological conditions due to disturbances of the central nervous system and disorders relating to the field of neuropsychiatry.

Hence, another object of the invention is to provide a method of treating central neurological disorders and including, in particular, convulsive states and seizures, and disorders relating to the field of neuropsychiatry in a host in need of such treatment, such method comprising the administration to said host of an effective dose of at least one ester of the invention.

Daily dosage will be preferably from 10 mg/kg to 50 mg/kg of the active principle of the invention when administered to a human being.

The compounds of the invention can be prepared following different procedures in accordance with their chemical structure.

I. Glycerol α-monoesters and 1,2,4-butanetriol α-monoesters (A) When these α-monoesters correspond to the general formula:

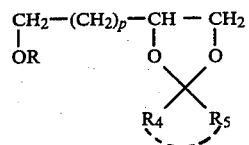

in which R, $R_4$, $R_5$ and p have the same meaning as given above, they can be prepared by reacting, under reflux, glycerol or 1,2,4-butanetriol and a ketone of the general formula:

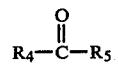

in which $R_4$ and $R_5$ have the same meaning as given above in the presence of p-toluenesulphonic acid as catalyst optionally in the presence of a solvent such as benzene to obtain a ketal of the general formula:

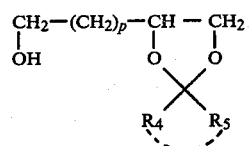

wherein $R_4$, $R_5$ and p have the same meaning as given above, which is further esterified in pyridine or in a mixture of dimethylformamide/pyridine at 65° C.±5° C. with the chloride of an acid of general formula I, to provide the required compound of the invention.

When the chloride of the acid of formula I is overloaded, the ketal of formula I will be previously reacted with sodium or sodium hydride in N,N-dimethylformamide and the esterification will be carried out in N,N-dimethylformamide or a N,N-dimethylformamide/hexamethylenephosphotriamide mixture at a temperature between 40° and 90° C.

(B) When these α-monoesters correspond to the general formula:

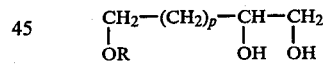

in which R and p have the same meaning as given above, they can be prepared by hydrolysing a ketal of formula III above, the reaction being conducted at room-temperature, in a hydromethanolic medium and in the presence of a diluted inorganic or organic acid such as hydrochloric acid, sulphuric acid or acetic acid to obtain the required compounds of the invention.

II. Glycerol β-monoesters

These esters which can be represented by the general formula:

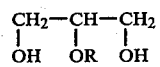

in which R has the same meaning as given above can be prepared by reacting glycerol with benzaldehyde in the presence of a water eliminator for example benzene or toluene and of p-toluenesulphonic acid as catalyst to obtain a mixture of about 90/10 of glycerol 1,2-benzylidene derivative and glycerol 1,3-benzylidene derivative.

When this mixture is maintained at low temperature i.e. at about 0° C. and in the presence of dry hydrochloric acid the 1,2-benzylidene derivative isomerises into the 1,3-benzylidene derivative.

The 1,3-benzylidene derivative in question is then esterified with the chloride of an acid of formula I at 60° C.±5° and in the presence of an acid acceptor such as pyridine to give a benzylidene derivative of the general formula:

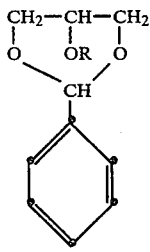
VIII wherein R has the same meaning as given above, which is then reacted with hydrogen in an alcoholic medium for example in ethanol and in the presence of palladium charcoal as catalyst, the reaction being conducted at atmospheric pressure and at room-temperature, to give the required compound of the invention.

In place of benzaldehyde, a derivative thereof substituted on the aromatic moiety can also be used.

III Glycerol diesters

These esters, which can be represented by the general formula:

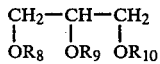
IX wherein one of the symbols $R_8$, $R_9$ and $R_{10}$ represents hydrogen and the other two represent a radical R as defined above, can be obtained as follows:

(A) Glycerol 1,2-diesters (a) When $R_8$ represents hydrogen and $R_9$ and $R_{10}$ are identical and represent a radical R by reacting a ketal of formula V in which p represents 0 with benzyl chloride in the presence of an alkali metal, for example sodium, to obtain the corresponding benzyl ether of the general formula:

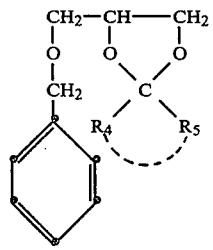
X wherein $R_4$ and $R_5$ have the same meaning as given above, the reaction being conducted under reflux and in an appropriate solvent such as toluene.

The benzyl ether so obtained is further hydrolysed in a water/acetic acid mixture at the reflux temperature of this mixture or in a hydromethanolic/hydrochloric acid mixture at room-temperature to provide 1-benzylglycerol which is then esterified with the chloride of an acid of formula I in the presence of an acid acceptor such as pyridine and at a temperature between 50° and 95° C. to obtain a diester of the general formula:

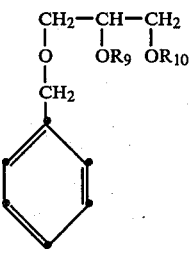
XI wherein $R_9$ and $R_{10}$ are identical and represent a radical R as defined above which is further reacted with hydrogen in an alcohol such as ethanol in the presence of palladium charcoal as catalyst, the reaction being conducted at atmospheric pressure and at room-temperature, to provide the required compounds of the invention.

When either of the radicals $R_9$ or $R_{10}$ is overloaded the compound of formula X will be prepared, preferably after sodation of 1-benzylglycerol with sodium hydride, the esterification taking place in N,N-dimethylformamide.

The glycerol 1,2-diesters of the invention wherein the radicals in the 1- and 2-positions are identical can also be prepared in accordance with other procedures.

Other methods have in fact been experimented in the particular case of glyceryl 1,2-bis-(di-n-propylacetate).

For example, glyceryl 1,2-bis-(di-n-propylacetate) can also be obtained by reacting epichlorhydrine with an alkali metal salt of di-n-propylacetic acid, for example the sodium salt, in an appropriate solvent such as for example water or a toluene/dimethylformamide mixture and at a temperature between 60° and 80° C. to obtain 2,3-epoxy-propyl di-n-propylacetate. This epoxy derivative is then reacted with di-n-propylacetic acid at a temperature between 60° and 80° C. in the presence of boron trifluoride, preferably in the form of its etherate, or in the presence of sulphuric acid which provides the required diester.

(b) When $R_8$ represents hydrogen and $R_9$ and $R_{10}$ are different and represent the radical R, by reacting epichlorhydrine with the alkali metal atom derivative, for example the sodium derivative, of an acid of formula I, the reaction being conducted in an appropriate solvent such as a toluene/dimethylformamide mixture and at a temperature between 60° and 80° C. to obtain an epoxy derivative of the general formula:

$$CH_2\text{---}CH\text{---}CH_2 \quad\quad XII$$
$$\phantom{CH_2}\diagdown O \diagup \phantom{CH_2} OR_{10}$$

wherein $R_{10}$ represents a radical R as defined above. This epoxy derivative is then reacted at a temperature between 60° and 80° C. with a different acid of formula I in the presence of boron trifluoride, preferably in the form of its etherate or in the presence of sulphuric acid which provides the required ester of the invention.

(B) Glycerol 1,3-diesters (a) When $R_8$ and $R_{10}$ are identical and represent the radical R and $R_9$ represents hydrogen by esterifying dihydroxyacetone with the chloride of an acid of formula I, this reaction being conducted under reflux in the presence of an acid acceptor such as pyridine and in an ether as solvent such as isopropyl ether, to obtain a ketodiester of general formula:

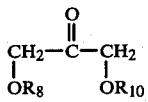   XIII wherein $R_8$ and $R_{10}$ represent a radical R as defined in formula I, which is reduced, at room-temperature, with potassium borohydride in an ether such as tetrahydrofuran. The complex so formed is then hydrolysed with a strong inorganic acid such as, for example, hydrochloric acid to provide the required compound of the invention.

(b) When $R_8$ and $R_{10}$ are different and represents the radical R as defined in formula I above and $R_9$ represents hydrogen, by esterifying a diol of general formula:

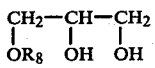   XIV wherein $R_8$ represents a radical R as defined in formula I above, with the chloride of an acid of formula I, the reaction being conducted between room-temperature and 110° C. and in an acid acceptor such as pyridine to obtain the required compound of the invention.

Preferably 1 to 1.5 equivalents of chloride of the acid of formula I will be reacted with 1 equivalent of diol of formula XIV.

Useful mixtures of esters of the invention containing a high precentage of diesters of the invention can be obtained in accordance with specific procedures.

In the particular case of glycerol di-n-propylacetic esters the following method can be used.

Esterification at a temperature between −5° C. and +10° C. of one equivalent of glycerol with two equivalents of di-n-propylacetic acid or two equivalents of its chloride in the presence of pyridine as an acid acceptor followed by rectification of the mixture of esters so obtained either by distillation under high vacuum or by molecular centrifugation or by gaseous phase chromatography provides a mixture of glycerol di-n-propylacetic acid esters in a yield of 73 to 74%.

This mixture comprises:
Di-n-propylacetic monoesters—$\leq 10\%$
Di-n-propylacetic 1,2- and 1,3-diesters—$\geq 88\%$
Di-n-propylacetic 1,2,3-triester, di-n-propylacetic acid, glycerol—$\leq 2\%$ and is referred to hereinafter as "Mixture A".

However, it has been found quite unexpectedly that mixtures of glyceryl 1,2-bis-(di-n-propylacetate)/1,3-bis-(di-n-propylacetate) can be obtained practically free from mono- and tri-esters by esterifying at a temperature between 100° and 110° C. and for 5 to 10 hours one equivalent of 1,3-dichloro-2-propanol with two equivalents, preferably in excess, of an alkali metal salt, preferably the sodium salt, of di-n-propylacetic acid in N,N-dimethylformamide as a solvent, followed by rectification of the mixture of esters so obtained, for instance by distillation under high vacuum, molecular centrifugation or gaseous phase chromatography, so providing a mixture of glycerol 1,2- and 1,3-corresponding diesters in a yield higher than 85%.

Using preferred reaction conditions, the mixture of such glycerol 1,2- and 1,3-diesters is obtained by reacting, at a temperature of 100° C. for 8 hours and in N,N-dimethylformamide, 1,3-dichloro-2-propanol with two equivalents of sodium di-n-propylacetate, preferably in an excess of about 5%, followed by rectification of the mixture of diesters so obtained, for example by distillation under high vacuum, molecular centrifugation or gaseous phase chromatography. This provides a mixture of glyceryl 1,2- and 1,3-bis-(di-n-propylacetate) in a yield of about 88 to 95%.

When such conditions of reaction are observed, a reproducible mixture of glyceryl 1,3-bis-(di-n-propylacetate)/1,2-bis-(di-n-propylacetate) is obtained in a ratio of about 1.43 to about 1.54.

This mixture comprises:
Glyceryl 1-monoester—$\leq 1\%$
Glyceryl 1,2- and 1,3-diesters—$\geq 98\%$
Glyceryl 1,2,3-triester, di-n-propylacetic acid, 1,3-dichloro-2-propanol—$\leq 1\%$ and is referred to hereinafter as "Mixture B".

The N,N-dimethylformamide can be used in amounts three to five times the total amount of the reagents in the aforesaid process without influencing the total yield in final mixture of diesters.

Furthermore, the starting sodium di-n-propylacetate can be either the latter as such in solid form or an aqueous solution of sodium di-n-propylacetate prepared "in situ" from di-n-propylacetic acid and a 50%-aqueous solution of sodium hydroxide.

It is evident that when such as aqueous solution of sodium di-n-propylacetate is used as starting-product, water is introduced into the reaction medium. If the volume of water so introduced is not higher than 5% of the volume of N,N-dimethylformamide the yield in final mixture of diesters is not affected.

The process so described for preparing a mixture of glyceryl 1,2- and 1,3-bis-(di-n-propylacetates) presents numerous advantages, the most valuable of which being the production of an isolated final mixture of high purity. The crude products contain no triester. After only one distillation the content of such a mixture in total diesters is $\geq 98\%$.

Thus, the mixture of glyceryl 1,2- and 1,3-bis-(di-n-propylacetates), more particularly the "Mixture B," is of high commercial value: it is easy to obtain, in a reproducible manner, substantially free of impurities and at low cost because no separation of the constituents is required.

Furthermore, this mixture together with "Mixture A" present pharmacological and pharmacokinetic actions of prime importance as is discussed further on.

IV Glycerol 1,2,3-triesters

These esters, which can be represented by the general formula:

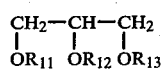   XV wherein $R_{11}$, $R_{12}$ and $R_{13}$ each represent a radical R as defined above can be obtained as follows:

(A) When $R_{11}$, $R_{12}$ and $R_{13}$ represent identical radicals R, by esterifying glycerol:
  either with an acid of formula I in excess at the reflux temperature of the medium and in the presence of p-toluenesulphonic acid as catalyst
  or with the chloride of an acid of formula I in excess at a temperature of 60°–70° C. and in the presence of an acid acceptor such as pyridine so as to obtain the required compound of the invention.

(B) When $R_{11}$ and $R_{12}$ represent identical radicals R and $R_{13}$ represents a different radical R, by esterifying a monoester of general formula:

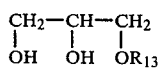  XVI wherein $R_{13}$ represents a radical R as defined in formula I with the chloride of an acid of formula I at a temperature between the room-temperature and 110° C. and in an acid acceptor such a pyridine to provide the required compounds of the invention.

(C) When $R_{11}$ and $R_{13}$ represent identical radicals R as defined in formula I and $R_{12}$, which is different, also represents a radical R as defined in formula I, by esterifying a diester of the general formula:

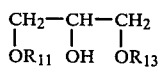  XVII wherein $R_{11}$ and $R_{13}$ are identical and represent a radical R as defined in formula I, with the chloride of an acid of formula I in the presence of an acid acceptor such as pyridine and at reflux temperature so as to obtain the required compound of the invention.

(D) When $R_{11}$, $R_{12}$ and $R_{13}$ all represent different radicals R as defined in formula I, by esterifying a diester of the general formula:

  XVIII wherein $R_{11}$ represents a radical R as defined in formula I and A represents a radical

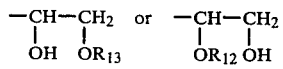

wherein $R_{12}$ and $R_{13}$ each represent a radical R as defined in formula I, with the chloride of an acid of formula I at the reflux temperature of the medium and in the presence of an acid acceptor such as pyridine, to give the required compounds of the invention.

V 1,2-Propanediol diesters, 1,3-propanediol diesters, 1,3-butanediol diesters, 1,4-butanediol diesters, 2-buten-1,4-diol diesters, 2-butyn-1,4-diol diesters, diethyleneglycol diesters, 1,2-cyclohexanediol diesters, thiodiglycol diesters, N-amidified diethanolamine diesters, trimethylolpropane triesters, glycerol triesters, 1,2,4-butane triol triesters, pentaerythritol tetraesters These esters can be represented by the general formula:

  XIX in which X represents a radical

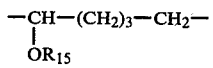

which forms a cyclohexylidene radical with the carbon atom to which it is attached, or a radical

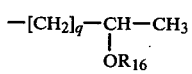

or a radical

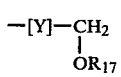

in which q represents 0 or 1 and Y represents $-CH_2-$, $-CH_2-CH_2-$, $-CH=CH-$, $-C\equiv C-$, $-CH_2-O-CH_2-$, $-CH_2-S-CH_2-$,

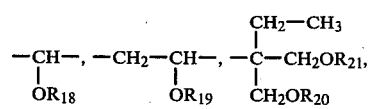

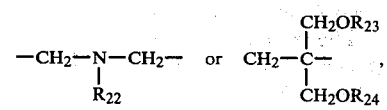

$R_{14}$ to $R_{24}$, each representing identical radicals R, can be obtained by esterifying in anhydrous pyridine the chloride of an acid of formula I with an alcohol of the general formula:

  XX in which X' represents a radical

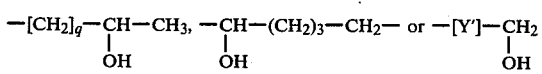

in which Y' represents a radical $-CH_2-$, $-CH_2-CH_2-$, $-CH=CH-$, $-C\equiv C-$, $-CH_2-O-CH_2-$, $-CH_2-S-CH_2-$,

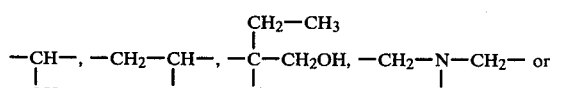

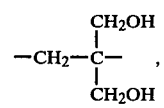

the esterification being conducted:

(a) at a temperature of 90° C. to obtain the required 1,2-propanediol diesters, 1,3-propanediol diesters, 1,4-butanediol diesters, diethyleneglycol diesters, 1,2-cyclohexanediol diesters, thiodiglycol diesters, and glycerol triesters (b) at a temperature between 0° C. and room-temperature to obtain the required 2-buten-1,4-diol diesters and 2-butyn-1,4-diol diesters (c) at a temperature between 20° C. and 30° C. to obtain the required 1,2,4-butanetriol triesters, trimethylolpropane triesters, pentaerythritol tetraesters and N-R-substituted-diethanolamine diesters.

The other compounds of the invention as well as other mixtures of compounds of the invention for instance other mixtures of glycerol 1,2- and 1,3-diesters can be obtained by means of known procedures or of processes described above, for instance by varying the molar amount of the starting-products.

The mixtures of mono-, di-, tri- and tetra-esters so obtained may then be separated using conventional procedures, for example by distillation under high vacuum, molecular centrifugation or gaseous phase chromatography, to obtain the required esters in pure form.

The starting chlorides of the acids of formula I can be obtained in accordance with known procedures by reacting the corresponding acid with thionyl chloride. Similarly, the alkali metal salts of these acids are obtained by reacting the acids in question with the hydroxide of the corresponding alkali metal.

The acids in question are either known compounds having been published in U.S. Pat. Nos. 3,325,361—3,958,011—4,025,649 and in Belgian Pat. No. 875,882 or compounds which can be obtained in accordance with procedures described in these patents.

The compounds of the invention have been found to possess valuable biochemical properties and in particular a marked competitive inhibitory effect with respect to the action of γ-aminobutyric α-ketoglutaric transaminase.

The esters of the invention also possess valuable neurotropic and psychotropic properties which manifest themselves to varying degrees. They comprise more particularly antianoxic, anticonvulsant, anxiolytic and antipsychotic properties. The esters of the invention can also act as regulators of the central nervous system and potentiators of central nervous system depressants.

These properties, when taken as a whole, are likely to render the compounds of the invention useful for treating various kinds of central neurological disturbances and disorders relating to the field of neuropsychiatry.

As an example of such central neurological disturbances or of disorders induced by central neurological dysfunction, the following may be cited: convulsive states and seizures such as, for example, epilepsy, choreic states such as Huntington's chorea, difficulties with respect to memory, balance and fixing the attention, as well as neurosis and psychosis of various origins.

Glycerol derivatives useful in the pharmaceutical field are already known.

In this connection, mention may be made of U.S. Pat. No. 3,686,238 which covers glycerol derivatives having enhanced and prolonged activity when orally administered.

Some of these glycerol derivatives consist in glycerol of which one hydroxyl is substituted by a drug moiety while one or both of the remaining hydroxyl groups are substituted by a natural fatty acid having from 8 to 24 carbon atoms.

It has now been found quite unexpectedly, in accordance with the present invention, that the slow-release of a drug moiety can be obtained from an ester formed from a therapeutically active acid of formula I above and a polyol, preferably glycerol, without any need to substitute at least one OH of the polyol with a natural fatty acid.

This invention could not be suggested by or deduced from the prior art.

The compounds of the present invention represent a progress with regard to the esters of the prior art in that no natural fatty acid is included within the molecule of the esters of the invention. A step in synthesis is thus eliminated i.e. the substitution of one or two hydroxyl groups of the glycerol by a fatty acid. The compounds of the invention are therefore more simple in structure than those of the prior art.

It appears thus that the fatty acyl radical included within the molecule of the esters of U.S. Pat. No. 3,686,238 offers no particular advantages. This acyl radical seems only to play the role of a vehicle together with the glycerol supporting the drug moiety.

Furthermore, attention must be drawn to the fact that none of the drug moieties disclosed in the above-cited U.S. Patent is included within the scope of the acids of formula I above.

Moreover, no proof of preparation and usefulness of the derivatives of U.S. Pat. No. 3,686,238 is given therein whereas this patent generically covers thousands of compounds.

Hydrolysis, in both animals and humans, of the esters of the invention thus releases a polyol and the acid corresponding to general formula I above. When the ester of the invention is a compound of formula III above or an epoxy derivative, it is evident that the alkylidene, the cyclohexylidene or the epoxy radical is also hydrolysed in the organism.

It has been observed that, as a result of this hydrolysis, the compounds of the invention can be regarded as a slow-release form of the acids in question which attains a long-lasting therapeutic level in the animal and/or in humans.

These acids, which can be represented by the general formula I above, are in fact, the pharmacological moiety in the compounds of the invention.

Some of these acids of formula I, and derivatives thereof, are already known neurotropic and psychotropic agents having been published as such in the patents cited above.

Esters of the invention were even found to be more valuable than the parent drug of formula I with respect to toxicity.

The esters of the invention which have been found to be especially useful in the treatment of central neurological disturbances and in particular epilepsy are those wherein the acyl radical corresponding to R in formula I represents a di-n-propylacetyl radical.

In humans, glyceryl 1,2-bis-(di-n-propylacetate) and glyceryl 1,3-bis-(di-n-propylacetate) were found to be of particular value together with the above-two described mixtures of these glyceryl diesters.

VI Pharmacological study

The results of trials performed with such di-n-propylacetyl derivatives in order to determine the anticonvulsant action are set out below.

A. Pentylenetetrazol-induced seizure

The anticonvulsant action was determined using pentylenetetrazol as convulsant agent.

Batches of 10 rats were treated by oral route with a dose of 600 mg/kg of glyceryl 1-(di-n-propylacetate).

At various times after administration, the animals received an intraperitoneal dose of 125 mg/kg of pentylenetetrazol.

The percentage of protection against the convulsive seizure was then determined at each of the times in question.

A similar trial was carried out with 100 mg/kg of di-n-propylacetic acid.

This dose represents the amount of di-n-propylacetic acid required to provide a di-n-propylacetic acid blood-level equivalent to the maximum level obtained with 600 mg/kg of glyceryl 1-(di-n-propylacetate). The results obtained are given in the following Table in which are shown the percentage of protection achieved at the various times indicated:

| Compound | Time in hours after the pentylenetetrazol injection | | | | | |
|---|---|---|---|---|---|---|
| | 0.5 | 1 | 2 | 4 | 8 | 16 |
| Glyceryl 1-(di-n-propylacetate) | 29 | 56 | 41 | 43 | 35 | 22 |
| di-n-Propylacetic acid | 23 | 0 | 0 | 0 | 0 | 0 |

B. Chronic cobalt-induced epilepsy

This trial was performed in comparison with sodium di-n-propylacetate. Batches of rats were given for 14 days either two daily intraperitoneal doses of 200 mg/kg (morning and evening) of sodium di-n-propylacetate or a daily intraperitoneal dose of 400 mg/kg (evening) of a mixture of glyceryl 1,2- and 1,3-bis-(di-n-propylacetates) ("Mixture A").

Electroencephalographic records were made each morning in comparison with control animals and the results are given below:

| | Controls | Sodium di-n-propylacetate | Mixture of diglycerides |
|---|---|---|---|
| Number of rats presenting at least one seizure | 7/7 | 3/4 | 0/2 |
| Number of seizures between the 7th and 14th day | 3.57 | 1.25 | 0 |

VII Pharmacokinetic study

Pharmacokinetic studies carried out with mono- and diesters of the invention wherein the radical R represents a di-n-propylacetyl radical have shown that these compounds present quite surprising differences in comparison with glyceryl tri-(di-n-propylacetate).

This latter product is a known compound having been disclosed by MEIJER and MEINARDI in "Clinical and Pharmacological aspects of sodium valproate (Epilim) in the treatment of epilepsy" pp. 71–74 (Proceedings of a Symposium held at Nottingham University, 23/24 Sept. 1975).

This triester was presented as "a remarkably useful substance which has all the properties expected of a slow-release preparation".

Likewise, J. W. A. MEIJER and R. KALFF also reached the conclusion, at the Symposium of BETHEL (1974—Federal Republic of Germany—"Antiepileptic Drugs" p. 222 to 228 edited by Schneider-Heidelberg), that glyceryl tri-(di-n-propylacetate) can act as a slow-release form of di-n-propylacetic acid. They showed that the maximum blood-level in di-n-propylacetic acid obtained after the oral administration to a human being of a dose of glyceryl tris-(di-n-propylacetate) equivalent to 600 mg of di-n-propylacetic acid is about 30 µg/ml, 8 hours after administration.

However, glyceryl tri-(di-n-propylacetate) cannot constitute a valuable therapeutic agent since the mean blood-levels in di-n-propylacetic acid attained therewith are from 10 to 20 µg/ml i.e. too low to provide therapeutic blood-levels.

Trials were performed with glyceryl tri-(di-n-propylacetate) within the framework of the study carried out in connection with the present invention.

These trials in which rats were given 600 mg/kg by oral route of the triester in question showed that di-n-propylacetic acid did not appear in the blood until 150 minutes after administration and that the maximum blood-levels in this acid did not exceed 10 µg/ml. The poor bioavailability of this triglyceride is probably due to the unsatisfactory metabolism of this product to glycerol and di-n-propylacetic acid.

From these results it is evident that glyceryl tri-(di-n-propylacetate) is of no value as a slow-release form of di-n-propylacetic acid in spite of the fact that this triester has been presented as a slow-release form in the literature.

In the course of pharmacokinetic trials with animals, it was discovered that glyceryl 1-(di-n-propylacetate), glyceryl 1,2-bis-(di-n-propylacetate) and glyceryl 1,3-bis-(di-n-propylacetate) possess the requisite qualities to enable di-n-propylacetic acid to be released in the animal organism at a decreasing rate.

This acid, which is also known as valproic acid, and salts thereof, is one of the best antiepileptic agents known at present and is widely marketed for this purpose.

However, it has further quite surprisingly and unexpectedly been observed that, amongst the esters of glycerol and di-n-propylacetic acid, only the diesters namely glyceryl 1,2-bis-(di-n-propylacetate) and glyceryl 1,3-bis-(di-n-propylacetate) can provide the slow-release of di-n-propylacetic acid in the human body to a degree which enables therapeutic blood-levels in this acid to be attained.

The blood-levels in di-n-propylacetic acid obtained after oral administration of 950 mg of glyceryl tri-(di-n-propylacetate) in humans were, in fact, too low and, in all cases, inferior to 20 µg/ml at the maximum blood-level attained whereas the therapeutic blood-levels required in this acid are between 50 and 100 µg/ml. i.e. between about 300 and 600 µmols/l.

This conclusion is in accordance with the results cited above and found by J. W. A. MEIJER and R. KALFF.

The poor bioavailability of this triglyceride is probably due to unsatisfactory metabolism of this compound, as was the case in the animal.

As regards glyceryl 1-(di-n-propylacetate), metabolism to glycerol and di-n-propylacetic acid was found to be too rapid.

The results obtained in pharmacokinetic studies undertaken with esters of the invention will be made clear by the description given hereunder with reference to the attached drawings.

A. Pharmacokinetic study in the animal

The first series of drawings represent blood-levels in acid of formula I above in relation to time, this acid being either released from a salt thereof or from an ester of the invention.

FIG. 1: represents blood-levels in di-n-propylacetic acid obtained from:
 (a) An oral dose to rats of 600 mg/kg of either:
  glyceryl 1-(di-n-propylacetate) (Curve 1)
  or glyceryl 1,2-bis-(di-n-propylacetate) (Curve 2)
  or glyceryl 1,3-bis-(di-n-propylacetate) (Curve 3)
 (b) An intravenous dose to rats of 200 mg/kg of sodium di-n-propylacetate (Curve 4)

The curves show that, in the animal, glyceryl 1-(di-n-propylacetate) when metabolized to di-n-propylacetic acid resists the rapid elimination of this acid and maintains a high blood-level in this acid.

Furthermore, the pharmacokinetic behaviour of these two diesters is very similar. The blood-levels in di-n-propylacetic acid obtained from these esters are very similar to those observed from the 2nd to the 24th hour after the injection of sodium di-n-propylacetate.

Figure 2:
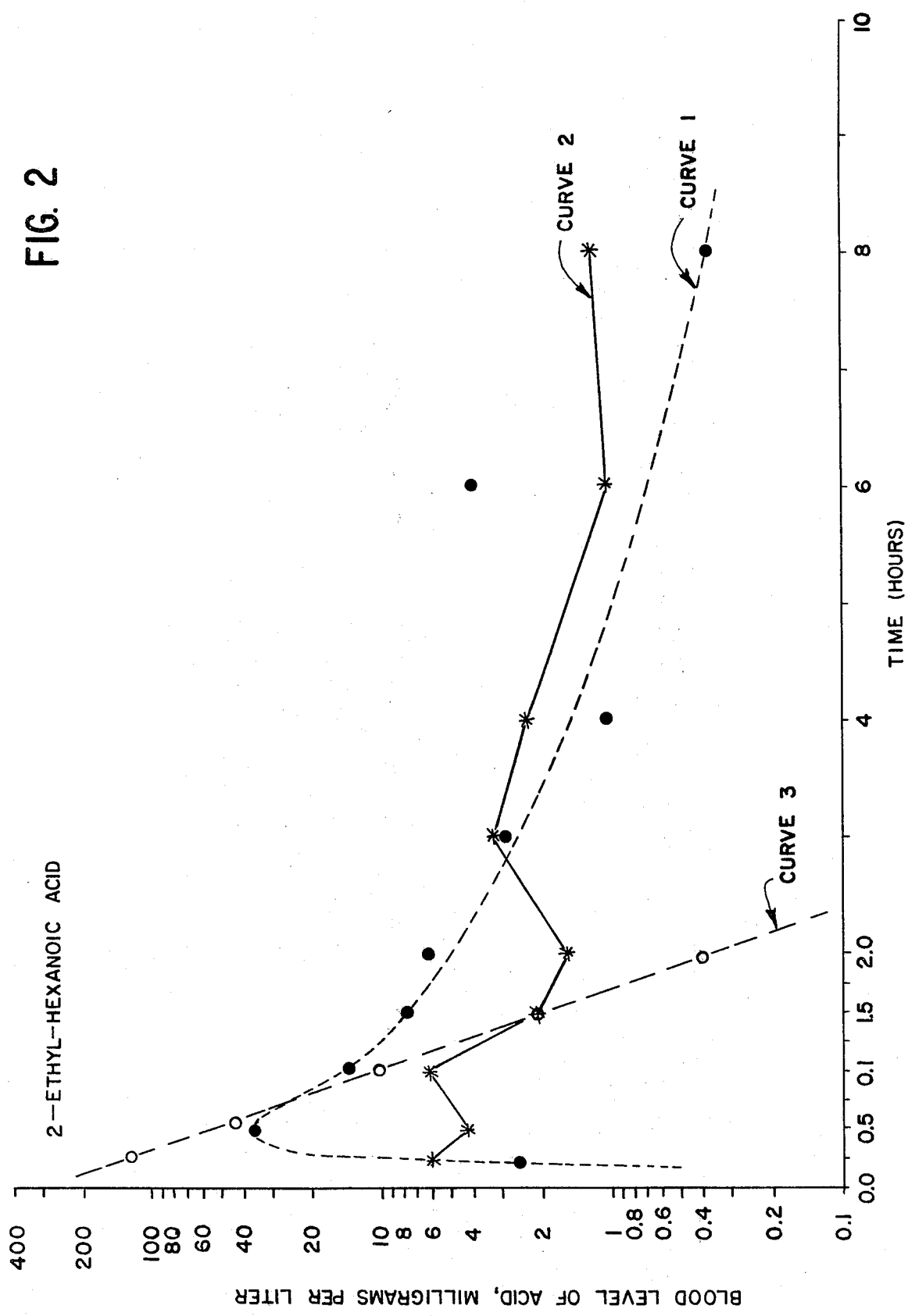

FIG. 2: represents blood-levels in 2-methyl-2-ethyl-hexanoic acid obtained from:
 (a) An oral dose to rabbits of:
  596 mg/kg of glyceryl 1-(2-methyl-2-ethylhexanoate) (Curve 1)
  207 mg/kg of glyceryl 1,2-bis-(2-methyl-2-ethylhexanoate) (Curve 2)
 (b) An intravenous dose to rabbits of:
  82 mg/kg of sodium 2-methyl-2-ethylhexanoate (Curve 3)

Figure 3:
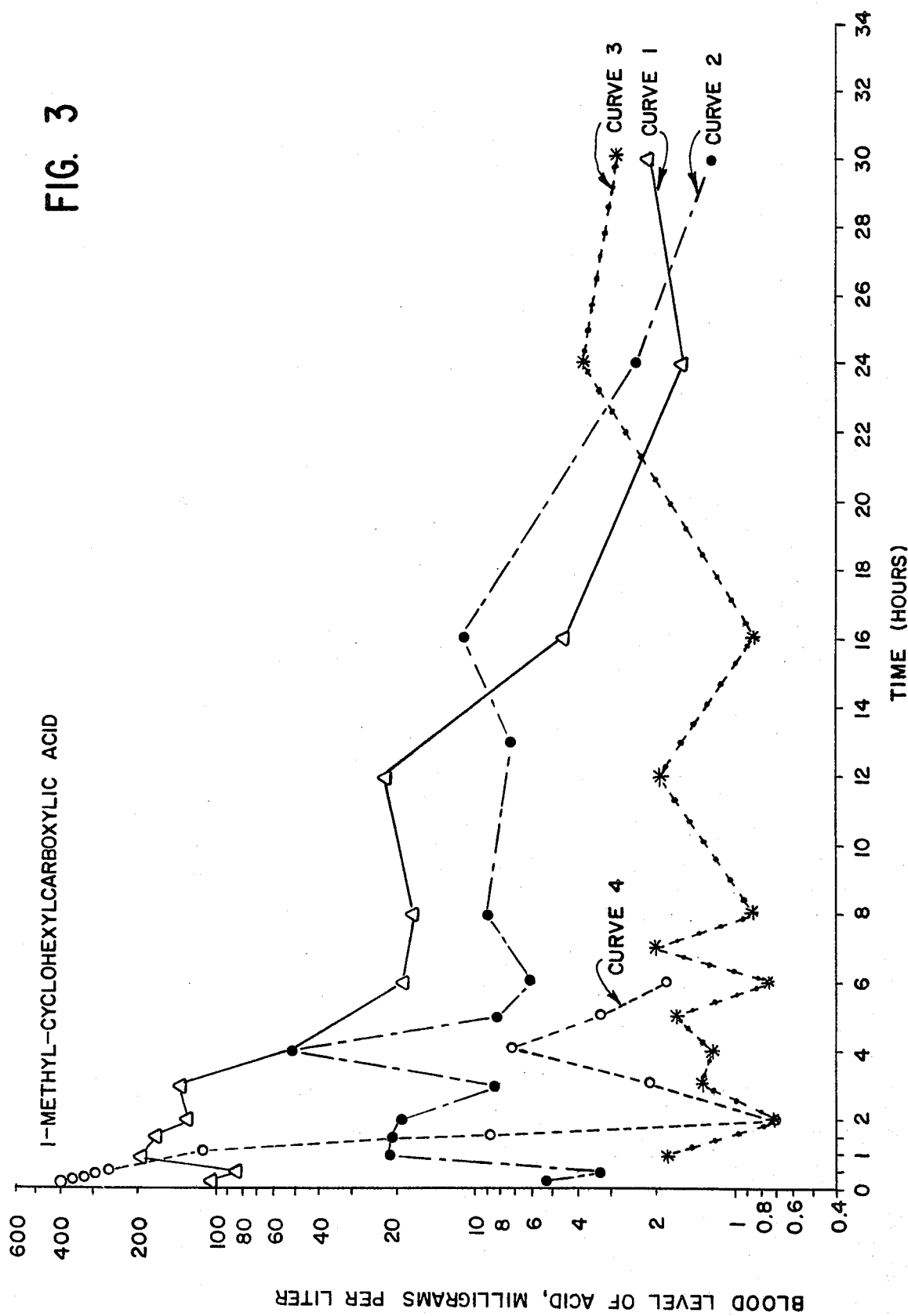

FIG. 3: represents blood-levels in 1-methyl-cyclohexylcarboxylic acid obtained from:
 (a) An oral dose to rats of 600 mg/kg of either:
  glyceryl 1-(1-methyl-cyclohexylcarboxylate) (Curve 1)
  or glyceryl 1,2,-bis-(1-methyl -cyclohexylcarboxylate) (Curve 2)
  or glyceryl 1,2,3-tri-(1-methyl-cyclohexylcarboxylate) (Curve 3)
 (b) An intravenous dose to rats of 200 mg/kg of sodium 1-methylcyclohexylcarboxylate (Curve 4)

The results show that higher blood-levels in 1-methyl-cyclohexylcarboxylic acid are obtained with the monoglyceride than with the diglyceride, this latter being itself better metabolized to 1-methyl-cyclohexylcarboxylic acid than the triglyceride.

Figure 4:
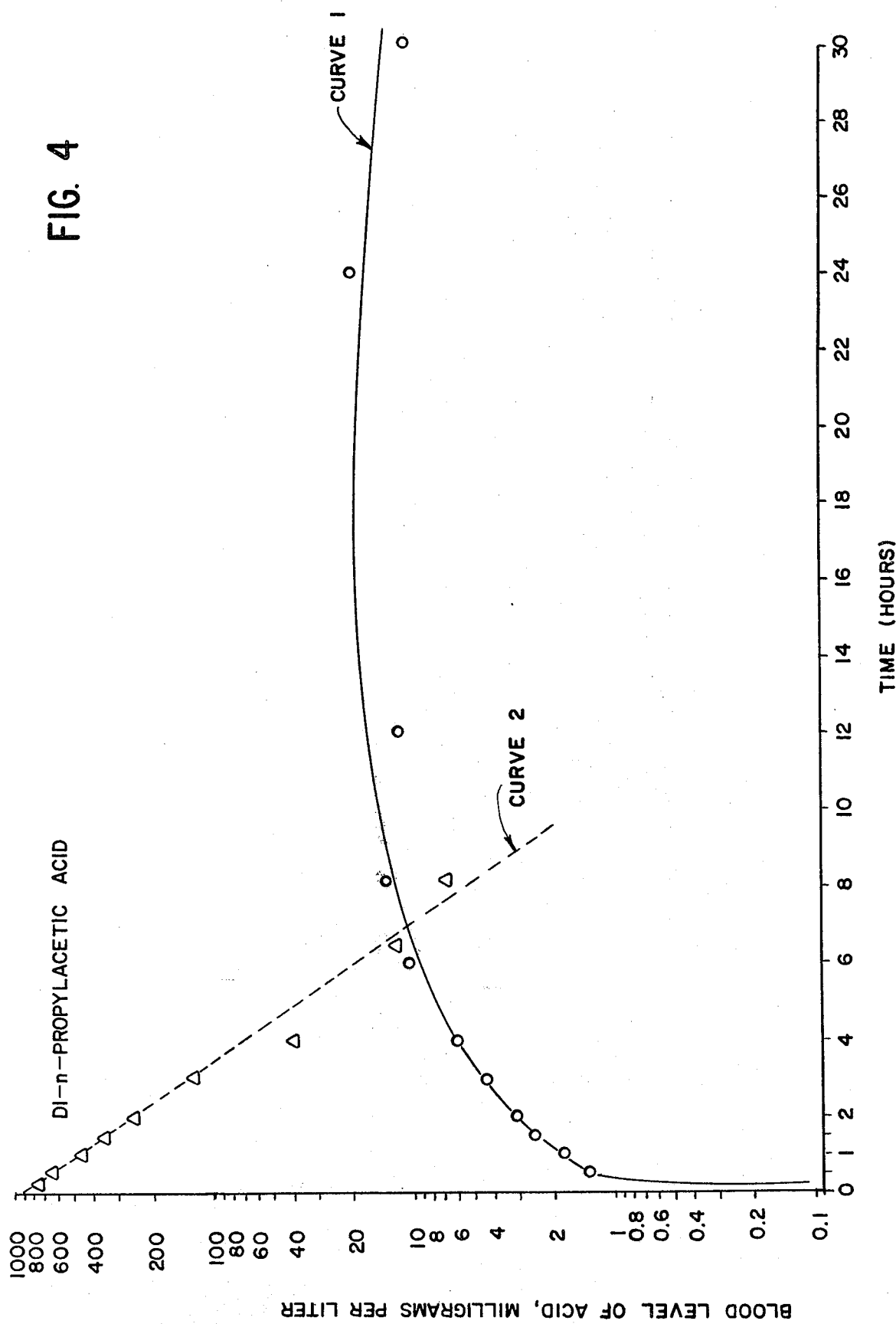

FIG. 4: represents blood-levels in di-n-propylacetic acid obtained from:
 (a) An oral dose to rabbits of 562 mg/kg of glyceryl 1-(di-n-propylacetate)-2-(1-methyl-cyclohexylcarboxylate) (Curve 1)
 (b) An intravenous dose to rabbits of 200 mg/kg of sodium di-n-propylacetate (Curve 2)

Figure 5:
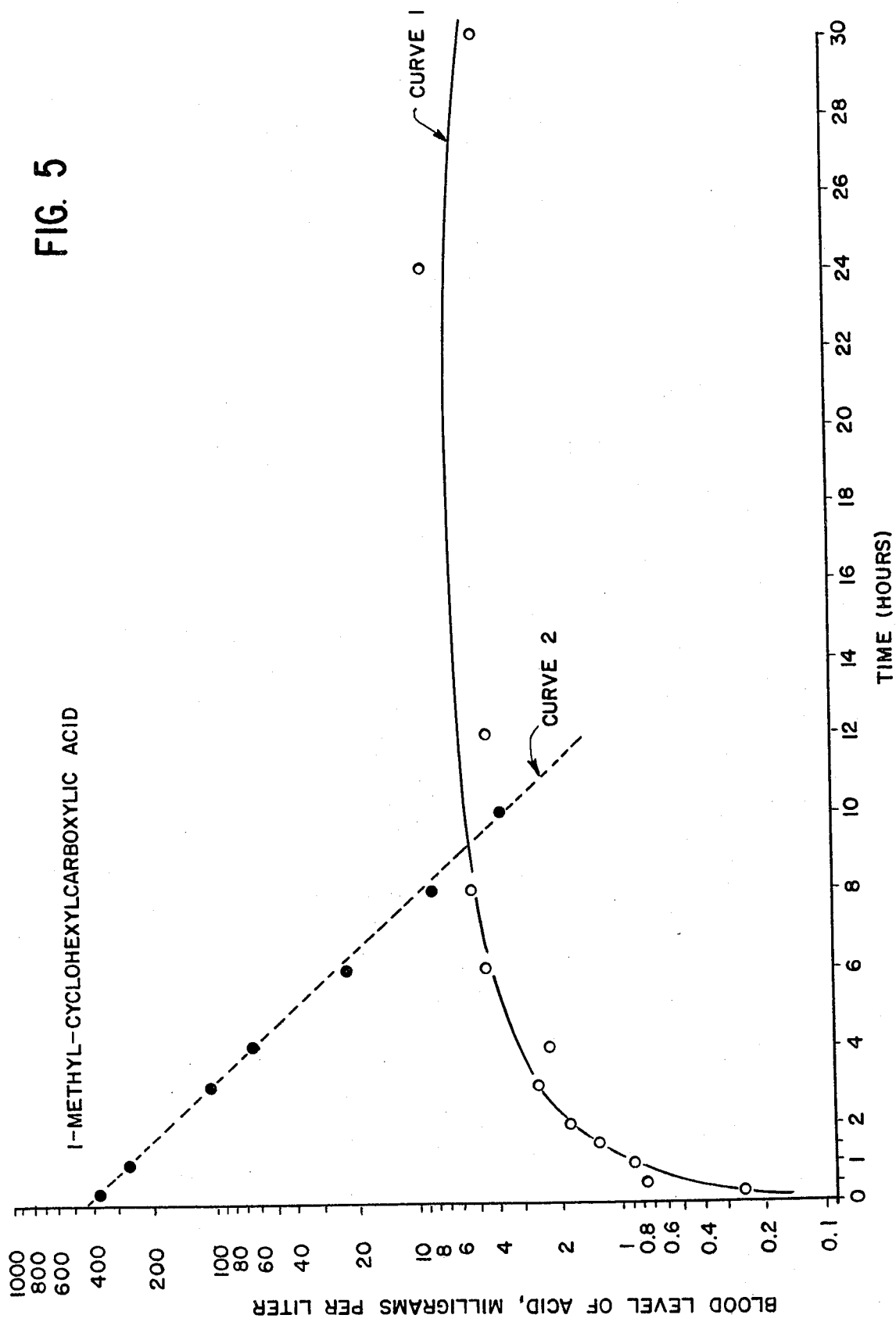

FIG. 5: represents blood-levels in 1-methyl-cyclohexylcarboxylic acid obtained from:
 (a) An oral dose to rabbits of 562 mg/kg of glyceryl 1-(di-n-propylacetate)-2-(1-methyl-cyclohexylcarboxylate) (Curve 1)
 (b) An intravenous dose to rabbits of 100 mg/kg of sodium 1-methyl-cyclohexylcarboxylate (Curve 2)

The results show that stable blood-levels in di-n-propylacetic acid and 1-methyl-cyclohexylcarboxylic acid can be maintained for at least 30 hours with the diglyceride.

Figure 6:
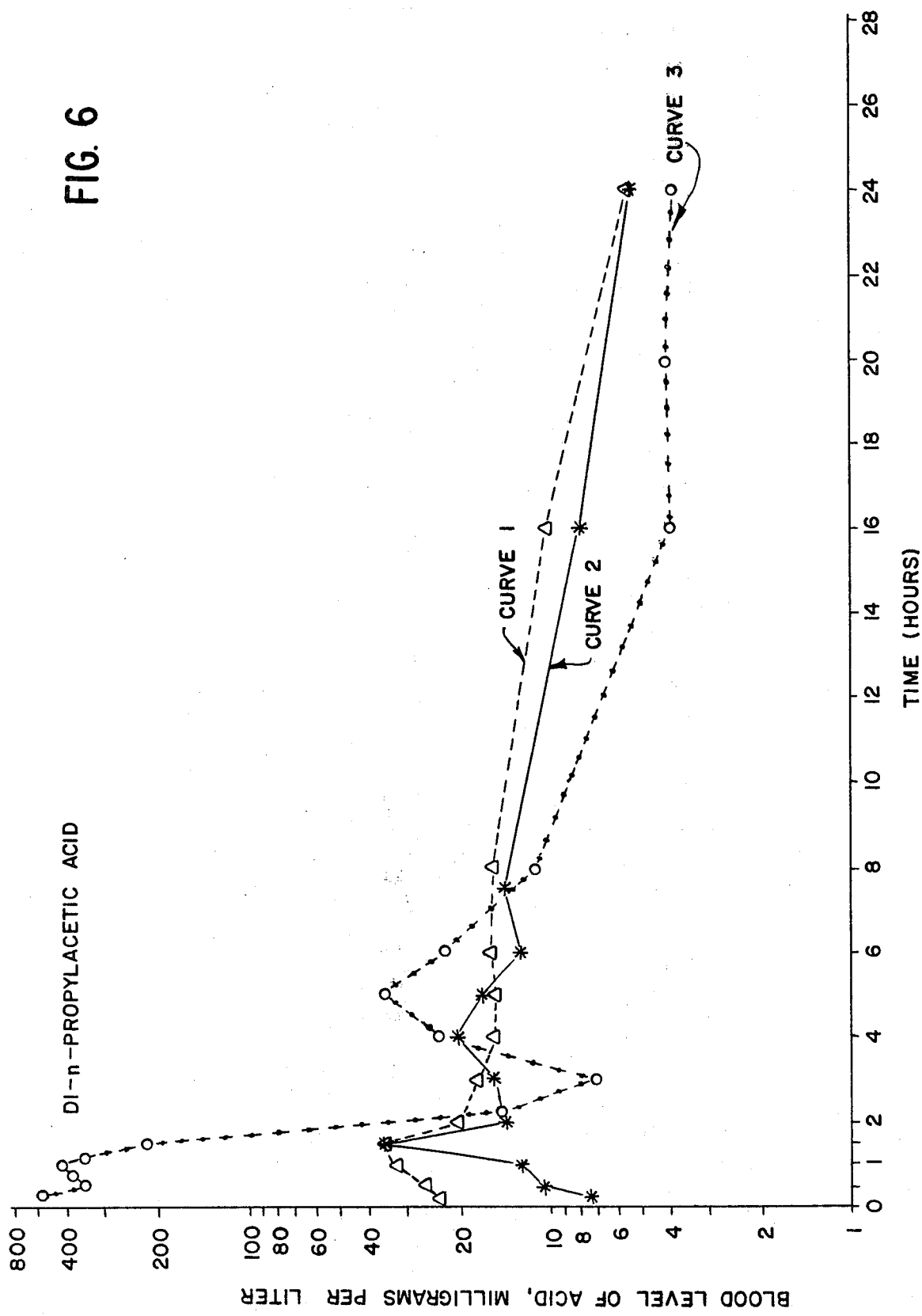

FIG. 6: represents blood-levels in di-n-propylacetic acid obtained from:
 (a) An oral dose to rats of 600 mg/kg of either:
  1,2-propanediol bis-(di-n-propylacetate) (Curve 1)
  or 1,3-propanediol bis-(di-n-propylacetate) (Curve 2)
 (b) An intravenous dose to rats of 200 mg/kg of sodium di-n-propylacetate (Curve 3)

From the results, it can be seen that relatively stable blood-levels in di-n-propylacetic acid can be obtained for at least 24 hours with the two diglycerides.

Figure 7:
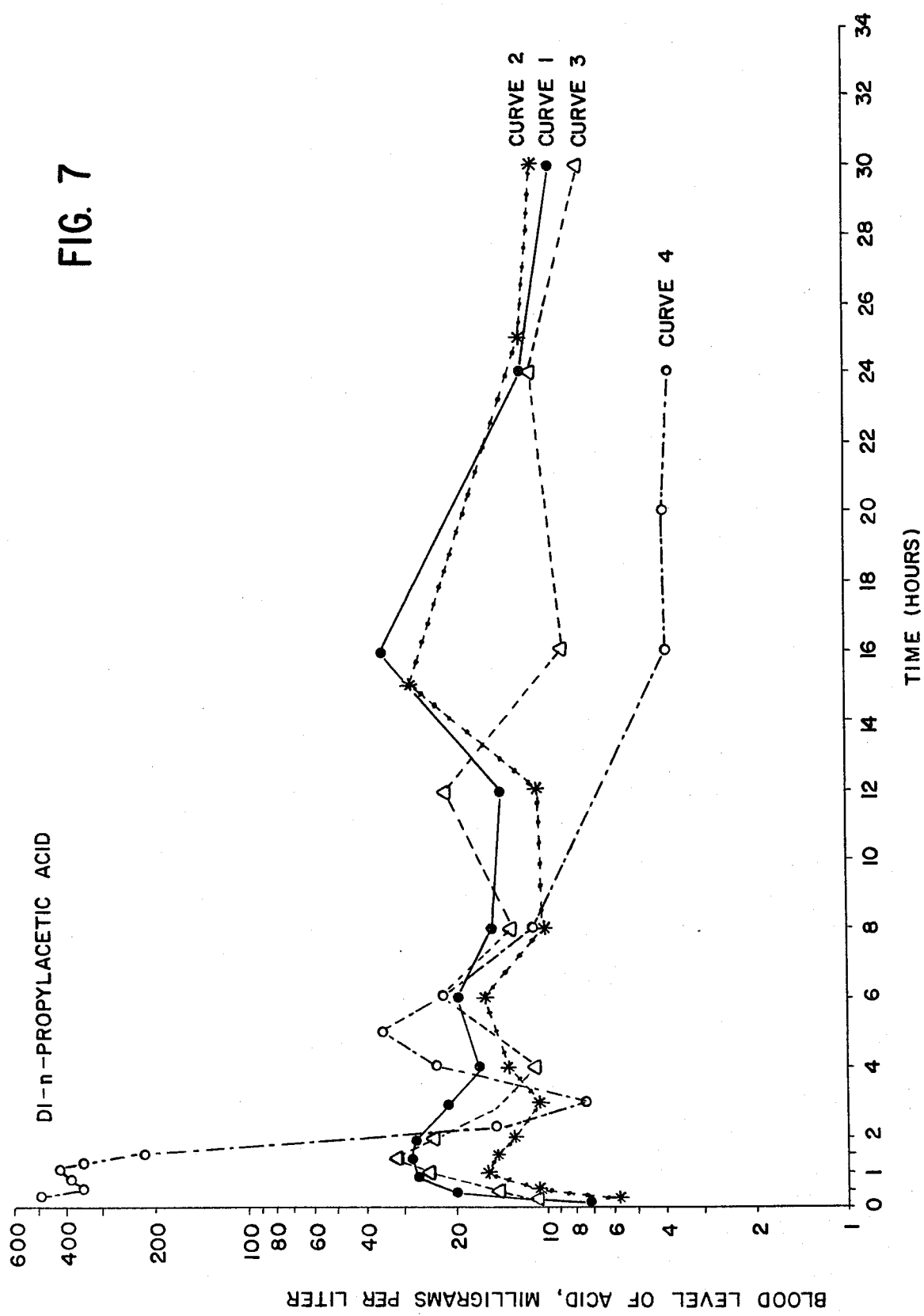

FIG. 7: represents blood-levels in di-n-propylacetic acid obtained from:
 (a) An oral dose to rats of 600 mg/kg of either:
  1,4-butanediol bis-(di-n-propylacetate) (Curve 1)
  or 2-buten-1,4-diol bis-(di-n-propylacetate) (cis isomer) (Curve 2)
  or 2-butyn-1,4-diol bis-(di-n-propylacetate) (Curve 3)
 (b) An intravenous dose to rats of 200 mg/kg of sodium di-n-propylacetate (Curve 4)

The results show that the metabolization of these three esters is more or less the same and leads to stable blood-levels in di-n-propylacetic acid for at least 30 hours.

B. Pharmacokinetic study in the human being

Figure 8:
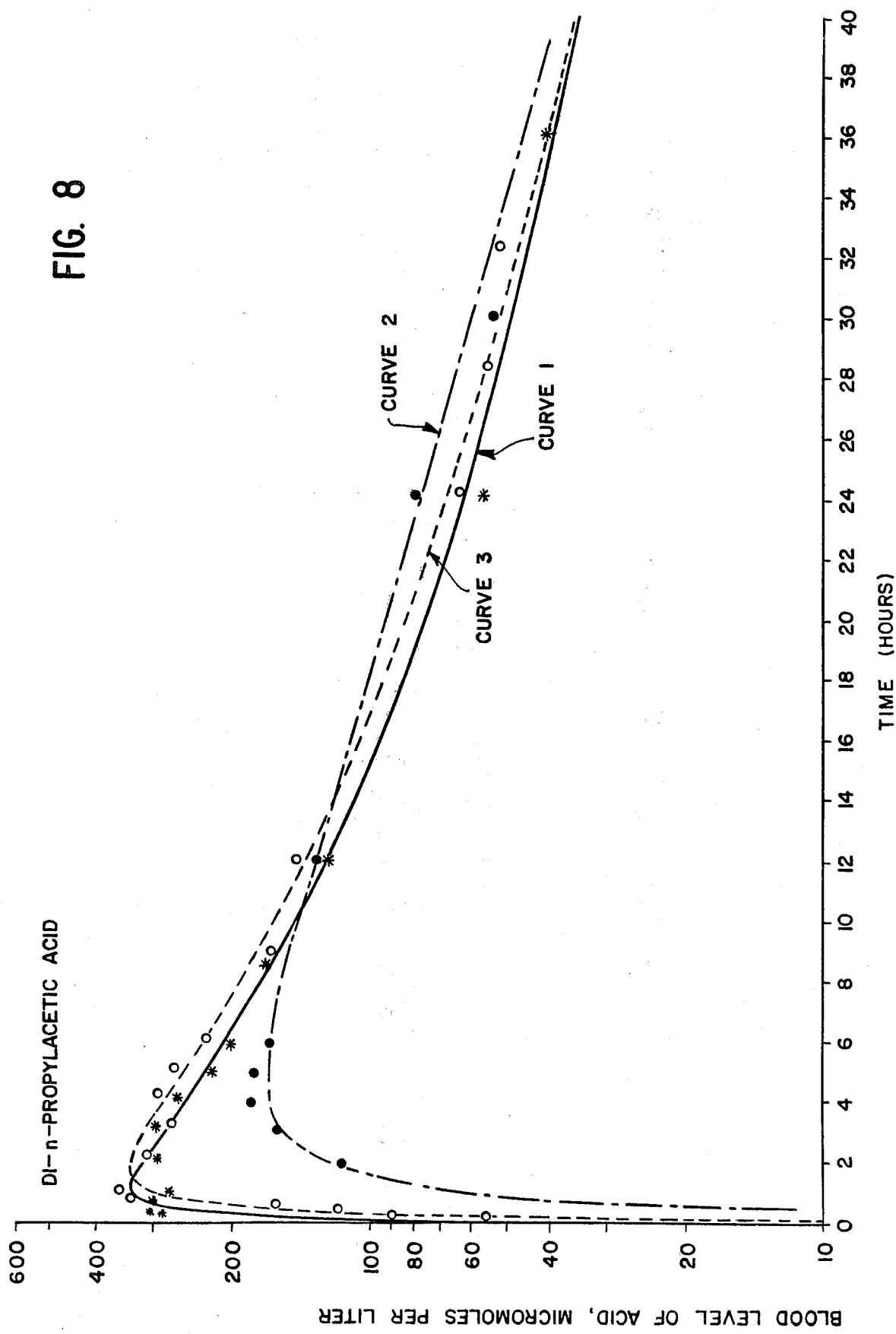

FIG. 8: represents blood-levels in di-n-propylacetic acid obtained from:
 (a) An oral dose of 600 mg of glyceryl 1-(di-n-propylacetate) (Curve 1)
 (b) An oral dose of 476 mg of glyceryl 1,2-bis-(-di-n-propylacetate) (Curve 2)
 (c) An oral dose of 460 mg of sodium di-n-propylacetate (Curve 3)

The results show that the blood-levels in di-n-propylacetic acid produced by the metabolism of glyceryl 1-(di-n-propylacetate) are very close to the blood-levels obtained after administration of sodium di-n-propylacetate (460 mg of sodium di-n-propylacetate are equivalent to 600 mg of glyceryl 1-(di-n-propylacetate) with respect to the amount of di-n-propylacetyl anion).

Therefore, the oral administration of 600 mg of glyceryl 1-(di-n-propylacetate) presented no advantage in comparison with 460 mg of sodium di-n-propylacetate.

This result proves that the monoester in question is quite unable to induce a slow-release in di-n-propylacetic acid in the blood.

Figure 9:
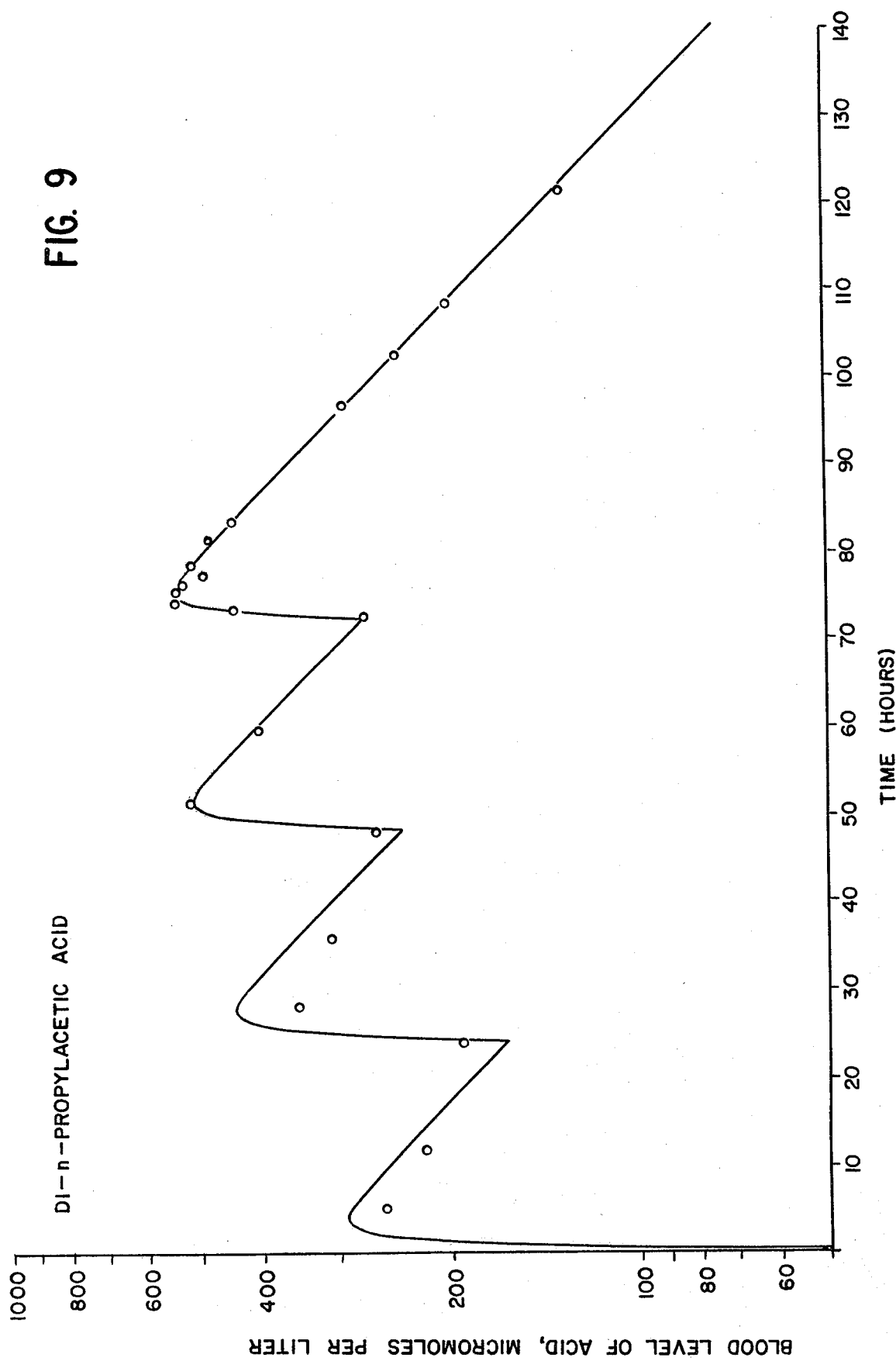

FIG. 9: represents the blood-levels in di-n-propylacetic acid obtained from the oral administration of 1000 mg of glyceryl 1,2-bis-(di-n-propylacetate) every 24 hours for 4 days.

The results show that the blood-levels in di-n-propylacetic acid varied from about 300 to 550 μmol/l (50 to 90 μg/ml).

This result proves that only one single oral administration of this 1,2-diester every 24 hours is capable of maintaining therapeutic blood-levels in di-n-propylacetic acid. This performance cannot be obtained with three oral administrations per day of sodium di-n-propylacetate each of 400 mg.

Very similar results have been obtained in the human being with glyceryl 1,3-bis-(di-n-propylacetate).

This compound even seemed to present better bioavailability than that of the corresponding 1,2-diester.

Figure 10:
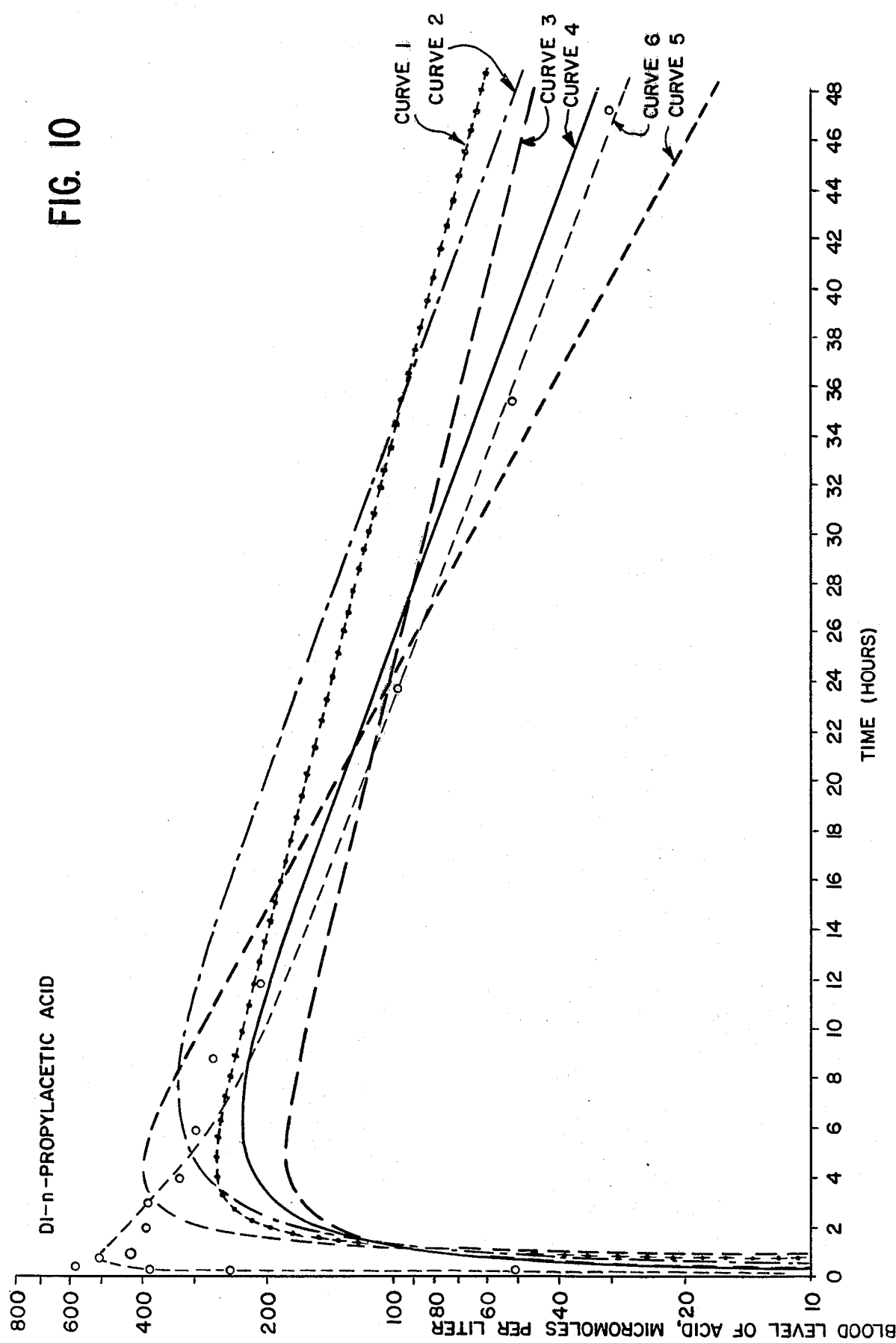

FIG. 10: represents the blood-levels in di-n-propylacetic acid obtained from:
 (a) An oral dose of 1000 mg of mixtures of glyceryl 1,2-bis-(di-n-propylacetate)/glyceryl 1,3-bis-(di-n-propylacetate)

("Mixtures A and B" referred to above) (Curves 1 to 5)

(b) An oral dose of 1000 mg of sodium di-n-propylacetate (Curve 6)

The results show that the kinetics of the release of di-n-propylacetic acid from the above-cited mixtures was very similar to those obtained with the 1,2-diester alone or the 1,3-diester alone. The apparent half-life of di-n-propylacetic acid released from these mixtures was found to be 20 h 20 min. whereas that of di-n-propylacetic acid after the oral administration the sodium salt of this compound was 11 h 35 min.

Figure 11:
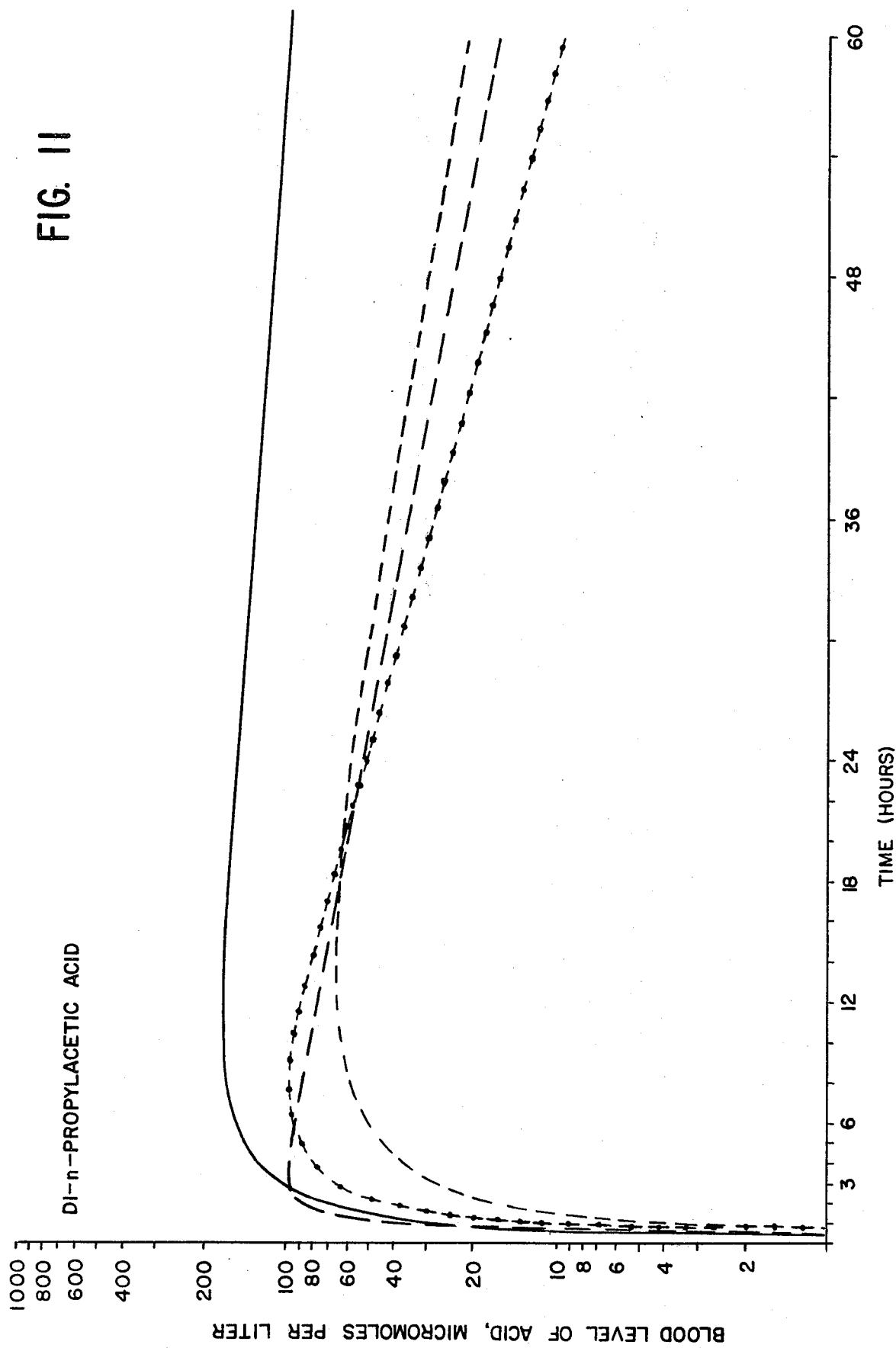

FIG. 11: represents the blood-levels in di-n-propylacetic acid obtained from an oral dose of 1000 mg of 1,2-propanediol bis-(di-n-propylacetate).

From the overall results of the above trials it can be concluded that glyceryl 1,2-bis-(di-n-propylacetate), glyceryl 1,3-bis-(di-n-propylacetate) and the mixtures of glycerol di-n-propylacetic esters as hereabove defined present, in the human being, marked advantages which can be summarized as follows:

The high blood-level in di-n-propylacetic acid appearing 30 min. to 1 hour after the oral administration of 300 to 500 mg of sodium di-n-propylacetate, which provokes undesirable side-effects, such as dizziness, can be avoided.

Dosage is rendered easier because one single daily administration i.e. about 500 mg/25 kg of body-weight/24 hours gives rise, from the fourth day after the first administration, to constant therapeutic blood-levels varying from 50 to 100 µg/ml of di-n-propylacetic acid. This advantage cannot be obtained with several daily administration of sodium di-n-propyl acetate as at present commercially available even when given in the known galenical slow-release form.

Therapeutic protection is better because the blood-level in di-n-propylacetic acid is more stable.

Furthermore, it has been demonstrated that the compounds of the invention are of extremely low toxicity.

The results of acute toxicity tests obtained with compounds of the invention are given below:

(a) Glyceryl 1,2-bis-(di-n-propylacetate)

$LD_0$ in rats by oral route: >5000 mg/kg
$LD_0$ in rats by intraperitoneal route: >2000 mg/kg
Similar results were obtained in mice.

(b) Glyceryl 1-(di-n-propylacetate)

$LD_{50}$ in rats by oral route: 2365 mg/kg
$LD_{50}$ in mice by oral route: 3361 mg/kg (c) Mixture of glyceryl 1,2-bis-(di-n-propylacetate)/glyceryl 1,3-bis-(di-n-propylacetate) ("Mixture A")

$LD_0$ in rats by oral route: >5000 mg/kg
$LD_{50}$ in rats by intraperitoneal route: 2368 mg/kg
$LD_0$ in mice by oral route: >5000 mg/kg
$LD_{50}$ in mice by intraperitoneal route: 2515 mg/kg (d) Mixture of glyceryl 1,2-bis-(di-n-propylacetate)/glyceryl 1,3-bis-(di-n-propylacetate) ("Mixture B")

$LD_0$ in rats by oral route: >5000 mg/kg
$LD_{50}$ in rats by intraperitoneal route: 2368 mg/kg
$LD_{50}$ in mice by oral route: 5597 mg/kg
$LD_{50}$ in mice by intraperitoneal route: 1920 mg/kg In comparison, the $LD_{50}$ of sodium di-n-propylacetate by oral route in rats and mice was found to be 1530 mg/kg and 1700 mg/kg respectively.

It will be appreciated that for therapeutic use the compounds of the invention will normally be administered in the form of a pharmaceutical or veterinary composition in a dosage unit form appropriate to the required mode of administration, the composition comprising as an essential active ingredient at least one compound of the invention in association with a pharmaceutical carrier or excipient therefor.

For oral administration, the composition may take the form of, for example, a hard- or soft-gelatin capsule, an aqueous emulsion, a drinkable ampoule or a microcapsule.

The composition may alternatively take the form of a solution or suspension for parenteral administration.

When in dosage unit form the composition may contain from 50 to 600 mg of active ingredient per dosage unit for oral administration.

The therapeutic composition will be prepared by associating at least one polyol ester of the invention with at least one appropriate carrier or excipient therefor for instance gelatin, glycerol, ethyl p-hydroxybenzoate (sodated), propyl p-hydroxybenzoate (sodated), titanium dioxide.

The following Examples illustrate the preparation of the polyol esters of the invention together with a therapeutic composition containing them:

EXAMPLE 1

Preparation of 1-(di-n-propylacetyl)-2,3-isopropylidene-glycerol or 2,2-dimethyl-4-(di-n-propylacetoxymethyl)-1,3-dioxolan (a) 1,2-Isopropylidene-glycerol Into a 1000 ml-flask were introduced 92.1 g (1 mol) of glycerol, 217 g (3.75 mol) of acetone, 179 g (275 ml) of petroleum ether and 2.75 g (0.015 mol) of p-toluenesulphonic acid. While stirring, the mixture was heated under reflux and the water so formed was eliminated up to the end of decantation.

This operation was performed in 25 to 30 hours. After cooling, the p-toluenesulphonic acid was neutralised by adding 1.20 g (0.009 mol) of potassium carbonate. Thirty minutes later, the medium was filtered while stirring. The filtrate was transferred into a 1000 ml-flask fitted with a condenser and the solvents were eliminated under atmospheric pressure to a temperature of 90° C. in the mass. The concentrate was distilled under reduced pressure and the fraction boiling at 86° C.±1° under 12 mm Hg was collected.

In this manner, 95 g of 1,2-isopropylidene-glycerol were obtained in the form of a colourless liquid.

Yield: 72%.

Using the same method as that described above the following compounds were prepared:

Compound

2-Methyl-2-ethyl-4-hydroxymethyl-1,3-dioxolan.
Yield: 54.7%.
$n_D^{20} = 1.4404$.
Infra-red spectrum (film): OH large at 3450 cm$^{-1}$, $CH_3$, $CH_2$ at 2990 cm$^{-1}$ (S), 2950 cm$^{-1}$ (S), 2890 cm$^{-1}$ (S), C—O—C large at 1060 cm$^{-1}$.

2-Methyl-2-isobutyl-4-hydroxymethyl-1,3-dioxolan.
Yield: 75.2%.

$n_D^{20} = 1.4432$.

Infra-red spectrum (film): OH large at 3450 cm$^{-1}$, CH$_3$, CH$_2$, CH at 3000 cm$^{-1}$, 2970 cm$^{-1}$ (S), 2940 cm$^{-1}$ (S), 2880 cm$^{-1}$ (S), C—O—C at 1045 cm$^{-1}$.

1,2-Cyclohexylidene-glycerol.
Yield: 35%.
$n_D^{21} = 1.4801$.

Infra-red spectrum (film): OH large at 3450 cm$^{-1}$, CH$_3$, CH$_2$ at 2950 cm$^{-1}$ (S), 2870 cm$^{-1}$ (m), C—O—C at 1100 cm$^{-1}$ (S).

1,2-Isopropylidene-1,2,4-butanetriol.
B.P.: 95° C. under 11 mm Hg.

(b) 1-(Di-n-propylacetyl)-2,3-isopropylidene-glycerol

Into a perfectly dry flask were introduced 132.2 g (1 mol) of 1,2-isopropylidene-glycerol, 118.7 g (1.5 mol) of pyridine and 271 g (290 ml) of N,N-dimethylformamide. While stirring, 162.7 g (1 mol) of di-n-propylacetyl chloride were introduced. This operation lasted 30 minutes. The reaction medium was heated to 65° C.±5° for 2 hours, cooled to room-temperature and hydrolsyed with 1200 g of distilled water. After this operation the mixture was extracted, while stirring for 30 minutes, with two fractions each of 700 g (528 ml) of methylene chloride. The organic fractions were collected and washed successively with 300 g of a 5%-aqueous solution of sodium bicarbonate and three fractions each of 300 g of distilled water. After decantation, the mixture was dried on sodium sulphate, filtered and rinsed with a minimum amount of methylene chloride. The solvent was eliminated under reduced pressure at a maximum temperature of 50° C. The concentrate was distilled under reduced pressure and the fraction boiling at 93° C.±2° under 1 mm Hg was collected.

In this manner 224.5 g of 1-(di-n-propylacetyl)-2,3-isopropylidene-glycerol were obtained in the form of a colourless liquid.
Yield: 87%.
$n_D^{21} = 1.4344$.

Infra-red spectrum (film): CH$_3$, CH$_2$ at 2970 cm$^{-1}$ (S), 2940 cm$^{-1}$ (S), 2880 cm$^{-1}$ (m), Co ester at 1740 cm$^{-1}$ (S), 1175 cm$^{-1}$ (m), C—O—C at 1060 cm$^{-1}$.

Using the same method as that described above, the following compounds were prepared:

Compounds 1-(Di-n-propylacetyl)-2,3-cyclohexylidene-glycerol.
Yield: 74.7%.
$n_D^{21} = 1.4583$.

Infra-red spectrum (film): CH$_3$, CH$_2$ at 2950 cm$^{-1}$ (S), 2875 cm$^{-1}$ (S), Co ester at 1740 cm$^{-1}$ (S), 1770 cm$^{-1}$ (S), C—O—C at 1100 cm$^{-1}$ (S).

1-(Tri-n-propylacetyl)-2,3-isopropylidene-glycerol (after sodation of 1,2-isopropylidene-glycerol in excess and esterification at 88°/90° C. in N,N-dimethylformamide).
Yield: 88.7%.
$n_D^{22} = 1.4430$.

Infra-red spectrum (film): CH$_3$, CH$_2$ at 2970 cm$^{-1}$ (S), 2945 cm$^{-1}$ (m), 2880 cm$^{-1}$ (S), Co ester at 1735 cm$^{-1}$ (S), 1210 cm$^{-1}$ (S), C—O—C at 1145 cm$^{-1}$ (S).

1-(2-Ethylhexanoyl)-2,3-isopropylidene-glycerol.
Yield: 77.5%.
$n_D^{20} = 1.4341$.

Infra-red spectrum (film): CH$_3$, CH$_2$ at 2980 cm$^{-1}$ (S), 2950 cm$^{-1}$ (S), 2990 cm$^{-1}$ (m), Co ester at 1745 cm$^{-1}$ (S), 1175 cm$^{-1}$ (S), C—O—C at 1220 cm$^{-1}$ (S).

1-(1-Methyl-cyclohexylcarbonyl)-2,3-isopropylidene-glycerol.
Yield: 67.3%.
$n_D^{20} = 1.4562$.

Infra-red spectrum (film): CH$_3$, CH$_2$ at 3000 cm$^{-1}$ (m), 2950 cm$^{-1}$ (S), 2865 cm$^{-1}$ (m), CO ester at 1735 cm$^{-1}$ (S), 1165 cm$^{-1}$ (m).

1-(2-Methyl-2-ethylhexanoyl)-2,3-isopropylidene-glycerol (sodation of 1,2-isopropylidene-glycerol).
Yield: 74.3%.

Infra-red spectrum (film): CH$_3$, CH$_2$ at 2970 cm$^{-1}$ (S), 2895 cm$^{-1}$ (S), CO ester at 1735 cm$^{-1}$ (S), 1160 cm$^{-1}$ (S).

1-(Di-n-propylacetyl)-3,4-isopropylidene-1,3,4-butanetriol.
B.P.: 103°-108° C. under 0.5 mm Hg.

1-(Di-n-propylmethoxyacetyl)-2,3-isopropylidene-glycerol.

1-(5-n-Propyloctanoyl)-2,3-isopropylidene-glycerol.

EXAMPLE 2

Preparation of glyceryl 1-(di-n-propylacetate)

Into a flask were introduced 258.4 g (1 mol) of 1-(di-n-propyl-acetyl)-2,3-isopropylidene-glycerol, 410 g (520 ml) of methanol and 125 ml of 3 N-hydrochloric acid. The reaction medium was maintained under stirring at room-temperature for about 3 hours. After this operation, the solvents were eliminated without going beyond 40° C. in the mass. The concentrate was transferred into a dropping-funnel and extracted with two fractions each of 860 g (650 ml) of methylene chloride. The extracts were collected and washed successively with 2 fractions each of 390 ml of a 5%-aqueous solution of sodium bicarbonate and 2 fractions each of 400 ml of distilled water. After drying on sodium sulphate, the mixture was filtered. The solvent was evaporated out at a temperature inferior to 50° C. and then under vacuum of about 1 mm Hg to constant weight. In this manner, 203 g of glyceryl 1-(di-n-propylacetate) were obtained in the form of a nearly colourless liquid.
$n_D^{20} = 1.4513$ Infra-red spectrum (film): OH large at 3470 cm$^{-1}$, CH$_3$, CH$_2$ at 2970 cm$^{-1}$ (S), 2950 cm$^{-1}$ (S), 2890 cm$^{-1}$ (S), CO ester at 1740 cm$^{-1}$ (S), shoulder at 1720 cm$^{-1}$, 1180 cm$^{-1}$ (m).

Using the same method as that described above, the following compounds were prepared:

Compound

Glyceryl 1-(tri-n-propylacetate).
Yield: 92%.
$n_D^{20} = 1.4561$.

Infra-red spectrum (film): OH large at 3430 cm$^{-1}$, CH$_3$, CH$_2$ at 2965 cm$^{-1}$ (S), CH at 2880 cm$^{-1}$ (S), CO ester at 1730 cm$^{-1}$ (S), 1215 cm$^{-1}$ (S).

Glyceryl 1-(2-ethylhexanoate).
Yield: 95%.
$n_D^{22} = 1.4511$.

Infra-red spectrum (film): OH large at 3530 cm$^{-1}$, CH$_3$, CH$_2$ at 2970 cm$^{-1}$, 2945 cm$^{-1}$, 2880 cm$^{-1}$, CO ester at 1740 cm$^{-1}$ (S), shoulder at 1725 cm$^{-1}$, 1180 cm$^{-1}$ (m).

Glyceryl 1-(1-methyl-cyclohexylcarboxylate).
Yield: 87%.
$n_D^{20} = 1.4769$.

Infra-red spectrum (film): OH large at 3420 cm$^{-1}$, CH$_3$, CH$_2$ at 2940 cm$^{-1}$ (S), 2865 cm$^{-1}$ (S), CO ester at 1725 cm$^{-1}$ (S), 1170 cm$^{-1}$ (S).

Glyceryl 1-(2-ethyl-2-methylhexanoate).
Yield: 92%.
$n_D^{22.5} = 1.4532$.

Infra-red spectrum (film): OH large at 3420 cm$^{-1}$, CH$_3$, CH$_2$ at 2970 cm$^{-1}$ (S), 2940 cm$^{-1}$ (S), 2880 cm$^{-1}$ (m), CO ester at 1730 cm$^{-1}$ (S).

1-(Di-n-propylacetoxy)-3,4-butanediol.
Yield: 64%.
$n_D^{19} = 1.4528$.

Infra-red spectrum (film): OH at 3400 cm$^{-1}$ (S), C=O at 1740 cm$^{-1}$ (S), CO ester at 1170 cm$^{-1}$ (m).

Glyceryl 1-(di-n-propylmethoxyacetate).
Yield: 40.5%.
$n_D^{14} = 1.4593$.

infra-red spectrum (film): OH at 3400 cm$^{-1}$ (S), C=O at 1755 cm$^{-1}$ (S), CO ester at 1200 cm$^{-1}$ (S).

Glyceryl 1-(4-n-propylheptanoate).
Yield: 42.6%.
$n_D^{20} = 1.4585$.

Infra-red spectrum (film): OH at 3400 cm$^{-1}$ (m), C=O at 1740 cm$^{-1}$ (S), CO ester at 1175 cm$^{-1}$ (m).

Glyceryl 1-(5-n-propyloctanoate).
Yield: 67.5%.
$n_D^{20} = 1.4995$.

Infra-red spectrum (film): OH at 3400 cm$^{-1}$ (S), C=O at 1740 cm$^{-1}$ (S), CO ester at 1170 cm$^{-1}$ (m).

EXAMPLE 3

Preparation of glyceryl 2-(di-n-propylacetate)

(a) 1,3-Benzylidene-glycerol or 2-phenyl-1,3-dioxan-5-ol

Into a 500-ml flask were introduced 92.1 g (1 mol) of glycerol, 78 g (100 ml) of benzene, 111.3 g (1.05 mol) of benzaldehyde and 0.2 g of p-toluenesulphonic acid.

While stirring, the mixture was refluxed and the water so formed was eliminated. This operation lasted about 4 hours. The solvent was then evaporated out under vacuum so that an oily residue of about 188 g was obtained.

This residue was distilled and the fraction boiling at 114±2° C. under 0.1 mm Hg was collected. After that, 0.35 g of gaseous hydrochloric acid was bubbled in the distillate. The medium was rendered homogeneous and allowed to stand for 8 days in a refrigerator.

After 12 hours at 0° C., a mass formed.

This mass was dissolved under heating in about 1075 g (1500 ml) of ethyl ether.

The organic layer was then washed with 70 ml of an aqueous ammonia solution (1% in NH$_3$), dried on sodium sulphate and crystallized at −5° C. After suction-filtration, the product was dried under vacuum at 40° C. to constant weight.

In this manner, about 81 g of 1,3-benzylidene-glycerol were obtained.
Yield: about 45%

(b) 1,3-Benzylidene-2-(di-n-propylacetyl)-glycerol

Into a flask, were introduced 180.2 g (1 mol) of crude 1,3-benzylidene-glycerol and 782.5 g (1.5 mol) of anhydrous pyridine.

While stirring, 244 g of di-n-propylacetyl chloride were added at room-temperature. This operation lasted 20 minutes. The mixture was then heated to 60° C. and maintained at this temperature for 2 hours.

The pyridine in excess was then eliminated at 50° C. under vacuum and the residue was taken up in 715 g (1000 ml) of ethyl ether. The medium was extracted with a 5%-aqueous solution of potassium carbonate to obtain a pH=7 to 8 and then with distilled water to obtain a ph=6 to 7. After drying on sodium sulphate, the mixture was filtered, the solvent was evaporated under vacuum and the extract so obtained was rectified by distillation. The fraction boiling between 150° and 152° C. under 0.5 mm Hg was collected.

In this manner 257 g of 1,3-benzylidene-2-(di-n-propylacetyl)-glycerol were obtained.
Yield: 83.9%.

(c) Glyceryl 2-(di-n-propylacetate)

Into a 2000 ml-flask were introduced 947 g (1200 ml) of absolute ethanol, 122.6 g (0.4 mol) of 1,3-benzylidene-2-(di-n-propylacetyl)-glycerol and 8 g of 5%-palladium charcoal. The apparatus was cleared with nitrogen. After that 18.8 l of hydrogen were bubbled at room-temperature and under normal pressure. This operation lasted 7 hours.

The apparatus was then cleared with nitrogen and the catalyst was filtered out. The filtrate was heated at a maximum of 50° C. and to constant weight under 1 mm Hg.

In this manner, 87.7 g of glyceryl 2-(di-n-propylacetate) were obtained in the form of a colourless slightly viscous liquid.
Yield: quantitative.
$n_D^{22} = 1.4512$.

Infra-red spectrum (film): OH large at 3450 cm$^{-1}$, CH$_3$, CH$_2$ at 2970 cm$^{-1}$ (S), 2950 cm$^{-1}$ (S), 2890 cm$^{-1}$ (m), CO ester at 1745 cm$^{-1}$ (S), 1720 cm$^{-1}$ (S), C—O at 1180 cm$^{-1}$ (m).

EXAMPLE 4

Preparation of glyceryl 1,2-bis-(di-n-propylacetate)

(a) 1-Benzyl-2,3-isopropylidene-glycerol

Into a perfectly dry 2000 ml-flask were introduced 500 g (575 ml) of toluene and 19.8 g (0.86 at.g.) of sodium.

The mixture was refluxed under vigorous stirring to obtain good dispersion of the sodium. After that, the medium was cooled while maintaining the vigorous stirring.

At a temperature, of +10°/+20° C., 132.2 g (1 mol) of 1,2-isopropylidene-glycerol were slowly added. This operation lasted about 30 minutes. The reaction medium was then heated to reflux for about 1 hour. After cooling at room-temperature, 108.9 g of benzyl chloride were added in one portion. The medium was progressively heated to reflux for about 1 hour and total reflux was maintained for 30 minutes. After cooling, the toluene was evaporated off under reduced pressure and 1070 g (1500 ml) of ethyl ether were added.

The salts were filtered out and rinsed with 360 g (500 ml) of ethyl ether. The solvent was eliminated under reduced pressure and the concentrate was rectified by destillation. The fraction boiling at 125° C.±2° under 3 mm Hg was collected.

In this manner, 166.7 g of 1-benzyl-2,3-isopropylidene-glycerol were obtained.
Yield: 75%.
B.P.: 117°–121° C. under 3 mm Hg.

(b) 1-Benzyl-glycerol

Into a flask were introduced 222.3 g (1 mol) of 1-benzyl-2,3-isopropylidene-glycerol and 567 g of a 10%-aqueous solution of acetic acid. While stirring, the mixture was heated on a water-bath (t°=95° C.) for 1 hour.

The solvents were eliminated under reduced pressure and the concentrate was rectified by distillation under vacuum. The fraction boiling between 132°–135° C. under 0.6 mm Hg was collected in the form of a colourless liquid.

In this manner, 160 g of 1-benzyl-glycerol were obtained.

Yield: 88%.

Infra-red spectrum (film): OH large at 3400 cm$^{-1}$, C—H aromatic 3080 cm$^{-1}$ (w), 3040 cm$^{-1}$ (m), CH$_3$, CH$_2$ 2930 cm$^{-1}$ (S), 2870 cm$^{-1}$ (S), C=C aromatic 1610 cm$^{-1}$ (w), 1590 cm$^{-1}$ (w).

(c) 1-Benzyl-2,3-bis-(di-n-propylacetyl)-glycerol

Into a 2000 ml-flask were introduced 182.2 g (1 mol) of 1-benzyl-glycerol and 978 g (1000 ml) of anhydrous pyridine.

While stirring at room-temperature, 341.2 g (2.1 mols) of di-n-propylacetyl chloride were slowly added. The medium was heated to 50°–55° C. and maintained at this temperature for 90 minutes. The pyridine in excess was eliminated under vacuum and the residue was taken up with 3000 g of distilled water. After extraction with two fractions each of 2500 ml of ethyl ether, the organic phase was successively washed with 3000 ml of a 7%-aqueous solution of hydrochloric acid, 3000 ml of distilled water, 3000 ml of a 10%-aqueous solution of sodium bicarbonate and three fractions each of 2000 ml of distilled water. The mixture was dried on sodium sulphate, filtered and the solvent was eliminated under vacuum. The crude product so obtained was purified by chromatography on a column containing 4350 g of silica using toluene as eluent.

In this manner, 355.2 g of crude 1-benzyl-2,3-bis(di-n-propylacetyl)-glycerol were obtained.

Yield: 81.7%.

Using the same method as that described above, the following compounds were prepared:

Compound

1-Benzyl-2,3-bis-(2-ethylhexanoyl)-glycerol.
Yield: 72%.
1-Benzyl-2,3-bis-(1-methyl-cyclohexyl-carbonyl)-glycerol.
Yield: 70%.
1-Benzyl-2,3-bis-(tri-n-propylacetyl)-glycerol.
Yield: 51.7%.
1-Benzyl-2,3-bis-(2-ethyl-2-methyl-hexanoyl)-glycerol.
Yield: 69.5%.

(d) Glyceryl 1,2-bis-(di-n-propylacetate)

Into an apparatus for hydrogenation were introduced 4350 ml of pure ethanol 434.3 g (1 mol) of 1-benzyl-2,3-bis-(di-n-propylacetyl)-glycerol and 26 g of 5%-palladium charcoal. The apparatus was cleared with nitrogen and then hydrogen was bubbled for 9 hours at room-temperature and under atmospheric pressure (22.4 l of hydrogen at 0° C./760 mm Hg). The apparatus was again cleared with nitrogen and the catalyst was filtered out. The filtrate was heated at 50° C. and then under vacuum (1 mm Hg) to dryness.

In this manner, 344 g of glyceryl 1,2-bis-(di-n-propylacetate) were obtained in the form of a colourless liquid.

Yield: quantitative.
$n_D^{20} = 1.447$.

Infra-red spectrum (film): OH large at 3500 cm$^{-1}$, CH$_3$, CH$_2$ at 2995 cm$^{-1}$ (S), 2980 cm$^{-1}$ (S), 2880 cm$^{-1}$ (S), CO ester at 1745 cm$^{-1}$ (S), 1170 cm$^{-1}$ (S).

Using the same method as that described above, the compounds hereunder were prepared:

Compound

Glyceryl 1,2-bis-(2-ethyl-hexanoate).
Yield: quantitative.
$n_D^{20} = 1.4468$.

Infra-red spectrum (film): OH large at 3500 cm$^{-1}$, CH$_3$, CH$_2$ at 2975 cm$^{-1}$ (S), 2950 cm$^{-1}$ (S), 2890 cm$^{-1}$ (S), CO ester at 1745 cm$^{-1}$ (S), shoulder at 1725 cm$^{-1}$, 1175 cm$^{-1}$.

Glyceryl 1,2-bis-(1-methyl-cyclohexylcarboxylate).
Yield: quantitative.
$n_D^{20} = 1.4773$.

Infra-red spectrum (film): OH large at 3520 cm$^{-1}$, CH$_3$, CH$_2$ at 2940 cm$^{-1}$ (S), 2870 cm$^{-1}$ (S), CO ester at 1735 cm$^{-1}$ (S), 1175 cm$^{-1}$ (S).

Glyceryl 1,2-bis-(tri-n-propylacetate).
Yield: quantitative.
$n_D^{20} = 1.4561$.

Infra-red spectrum (film): OH large at 3500 cm$^{-1}$, CH$_3$, CH$_2$ at 2970 cm$^{-1}$ (S), 2950 cm$^{-1}$ (S), 2885 cm$^{-1}$ (S), CO ester at 1735 cm$^{-1}$ (S), 1210 cm$^{-1}$ (m).

Glyceryl 1,2-bis-(2-ethyl-2-methylhexanoate).
Yield: 78.7%.
$n_D^{22} = 1.4519$.

Infra-red spectrum (film): OH large at 3530 cm$^{-1}$, CH$_3$, CH$_2$ at 2975 cm$^{-1}$ (S), 2950 cm$^{-1}$ (S), 2890 cm$^{-1}$ (S), CO ester at 1735 cm$^{-1}$ (S), 1150 cm$^{-1}$ (S).

EXAMPLE 5

Preparation of glyceryl 1,3-bis-(di-n-propylacetate)

(a) 1,3-Bis-(di-n-propylacetoxy)-acetone

Into a perfectly dry flask were introduced 680 g (935 ml) of isopropyl ether, 173.7 g (2.2 mols) of anhydrous pyridine and 90.1 g (1 mol) of dihydroxyacetone. While stirring at room-temperature, 349.7 g (2.15 mols) of di-n-propylacetyl chloride were introduced in 30 minutes to 1 hour. The reaction medium was then refluxed at 65° C. and maintained at this temperature for 3 hours. After cooling, the mixture was hydrolyzed with 500 ml of iced distilled water. The organic layer was washed with a diluted hydrochloric acid solution to pH=1 and then with water to neutrality. After drying on sodium sulphate, the solvent was evaporated at 50° C. under vacuum.

The concentrate was rectified by distillation and the fraction boiling between 155°–160° C. under 0.2/0.3 mm Hg was collected.

In this manner, 205 g of crude 1,3-bis-(di-n-propylacetoxy)-acetone were obtained.

Yield: 60%.

(b) Glyceryl 1,3-bis-(di-n-propylacetate)

Into a flask were introduced 342.48 g (1 mol) of 1,3-bis-(di-n-propylacetoxy)-acetone, 2490 g (2800 ml) of tetrahydrofuran and 59.3 g (1.1 mol) of potassium borohydride. After that 880 g of distilled water and 110 g (1.1 mol) of 36%-hydrochloric acid were added so that the pH of the medium remained between 7 and 8.

This operation lasted about 1 hour.

If necessary the pH was ajusted to 7-8.

The medium was allowed to stand for 1 hour and then heated to dryness, care being taken to maintain the temperature below 45°-50° C. The residue was taken up in ethyl ether, washed with water to eliminate the salts, dried on sodium sulphate and heated to dryness. The residue was taken up in toluene and passed through a column containing about 3000 g of silica. The residual ketodiester was eluted with toluene and the desired product with chloroform. The chloroform fractions containing the desired compound were heated to dryness at a temperature inferior to 50° C. and then under vacuum care being taken not to go beyond 50° C. In this manner, 200 g of glyceryl 1,3-bis-(di-n-propylacetate) were obtained in the form of a pale yellow liquid.

Yield: 58%.

$n_D^{20} = 1.4472$.

Infra-red spectrum: OH large at 3500 cm$^{-1}$, CH$_3$, CH$_2$ at 2980 cm$^{-1}$ (S), 2950 cm$^{-1}$ (S), 2890 cm$^{-1}$ (S), CO ester at 1740 cm$^{-1}$ (S).

EXAMPLE 6

Preparation of glyceryl tri-(1-methyl-cyclohexylcarboxylate)

Into a 500 ml-flask, were introduced 269 g (275 ml) of pyridine and 18.2 g (0.2 mol) of glycerol. While stirring, 100 g (0.623 mol) of 1-methyl-cyclohexylcarbonyl chloride were added in about 15 minutes. The reaction medium was progressively heated to 65°/70° C. in one hour and maintained at this temperature for 3 hours. After this operation, the mixture was refluxed for 2 hours and then cooled. The pyridine in excess was eliminated under vacuum and at a temperature of 60° C. The pasty mass so obtained was taken up in 250 g of distilled water and extracted with two fractions, each of 250 ml, of ethyl ether. The organic extracts were collected and washed successively with diluted hydrochloric acid to pH=1, with water, with a 5%-aqueous solution of sodium carbonate to pH≧10 and finally with water to neutrality. After being dried on sodium sulphate, the mixture was heated to dryness and the oil so obtained was taken up in toluene and passed through a column containing 730 g of silica. The fraction corresponding to the pure triglyceride was taken up in about 500 ml of ethyl ether and this solution was treated with 3 g of active charcoal. After filtration, the solution was heated to dryness at a temperature of 60°-70° C. and under a pressure of 0.5-1 mm Hg.

In this manner, 50 g of glyceryl tri-(1-methyl-cyclohexylcarboxylate) were obtained in the form of a yellowish slightly viscous liquid.

Yield: 54%.

$n_D^{17} = 1.4812$.

Infra-red spectrum (film): CH$_2$ at 2940 cm$^{-1}$ (S), 2860 cm$^{-1}$ (m), CO ester at 1740 cm$^{-1}$ (S), 1205 cm$^{-1}$ (S), 1160 cm$^{-1}$ (S).

EXAMPLE 7

Preparation of glyceryl 1-(1-methyl-cyclohexylcarboxylate)-3-(di-n-propylacetate)

Into a perfectly dry flask, were introduced 1000 ml of pyridine and 218 g (1 mol) of glyceryl 1-(di-n-propylacetate).

While stirring, 240.8 g (1.5 mol) of 1-methyl-cyclohexylcarbonyl chloride were progressively added at room-temperature. After that, the medium was heated to 40° C. for 4 hours and then to 70° C. for 6 hours. After cooling, the reaction mixture was hydrolyzed by adding 5000 ml of distilled water. The medium was extracted with three fractions each of 1000 ml of ethyl ether. The ethereal fractions were collected and washed successively with distilled water, a 2%-aqueous solution of hydrochloric acid and again with distilled water. After drying on sodium sulphate, the ether was eliminated under reduced pressure care being taken to maintain the temperature at a maximum of 40° C.

The oil so obtained was then passed through a column containing silica and eluted with a hexane/ethyl ether mixture.

In this manner, 88 g of glyceryl 1-(1-methyl-cyclohexylcarboxylate)-3-(di-n-propylacetate) were obtained.

$n_D^{21} = 1.4608$.

Infra-red spectrum (film): OH at 3500 cm$^{-1}$ (m, w), C═O at 1740 cm$^{-1}$ (S), Using the same procedure as that described above, the following compound was prepared:

Compound

Glyceryl 1-(di-n-propylacetate)-3-(2-methyl-2-ethyl-hexanoate).

$n_D^{21} = 1.4490$.

Infra-red spectrum (film): OH at 3500 cm$^{-1}$ (w), CH$_3$, CH$_2$ at 2970 cm$^{-1}$ (S), 2940 cm$^{-1}$ (S), 2880 cm$^{-1}$ (S), CO ester at 1730 cm$^{-1}$ (S), 1150 cm$^{-1}$ (w).

EXAMPLE 8

Preparation of glyceryl 1-(di-n-propylacetate)-2,3-(1-methyl-cyclohexylcarboxylate)

This compound was obtained (199.2 g) in addition to glyceryl 1-(1-methylcyclohexylcarboxylate)-3-(di-n-propylacetate) in Example 7.

$n_D^{20} = 1.4669$.

Infra-red spectrum (film): CH$_3$, CH$_2$ at 2970 cm$^{-1}$, 2940 cm$^{-1}$ (S), 2870 cm$^{-1}$ (m), CO ester at 1740 cm$^{-1}$ (S), 1160 cm$^{-1}$ (m).

EXAMPLE 9

Preparation of glyceryl 1-(di-n-propylacetate)-2-(1-methyl-cyclohexylcarboxylate)

(a) 2,3-Epoxy-propyl di-n-propylacetate

Into a flask were introduced 70 g (0.48 mol) of di-n-propylacetic acid, 250 ml of toluene and 30 ml of N,N-dimethylformamide. After this operation, 40 g of 50%-aqueous solution of sodium hydroxide were added. This mixture was heated to 60°-80° C. and 138.7 g (1.5 mol) of epichlorhydrine were introduced. The reaction medium was maintained under stirring for 6 hours at 70°-80° C. and then concentrated in a rotary evaporator. After extraction with ethyl ether, the organic fractions were collected and distilled under 1 mm Hg.

The fraction boiling between 76° and 78° C. was collected.

In this manner, 2,3-epoxy-propyl-di-n-propylacetate was obtained in the form of a limpid colourless liquid.

$n_D^{21} = 1.4351$

Infra-red spectrum (film): CH₃, CH₂ at 2975 cm⁻¹ (S), 2950 cm⁻¹ (S), 2890 cm⁻¹ (S), CO ester at 1745 cm⁻¹ (S), 1180 cm⁻¹ (S),

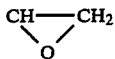

at 1260 cm⁻¹ (m).

(b) Glyceryl 1-(di-n-propylacetate)-2-(1-methyl-cyclohexylcarboxylate)

In a flask, 4 g (0.02 mol) of 2,3-epoxy-propyl-di-n-propylacetate and 5.6 g (0.04 mol) of 1-methyl-cyclohexylcarboxylic acid were heated at 70° C. for 90 minutes. After this, some drops of boron trifluoride etherate were added. The mixture was allowed to return to room-temperature and extracted with ethyl ether. The organic fractions were washed with sodium carbonate and the ether was evaporated off. The mixture of 1,2-and 1,3-diesters so obtained was then purified by chromatography on a column containing silica.

In this manner, glyceryl 1-(di-n-propylacetate)-2-(1-methyl-cyclohexylcarboxylate) was obtained.

EXAMPLE 10

Preparation of a mixture of glyceryl 1,2- and 1,3-bis-(di-n-propylacetates)

Into a perfectly dry flask were introduced 9.1 kg (9.3 l) of pyridine and 1.229 kg (13.36 mols) of glycerol.

Under vigorous stirring, the mixture was cooled to 0°/−5° C. After that, 4.340 kg (26.72 mols) of di-n-propylacetyl chloride were added, care being taken to maintain the reaction medium below 10° C. This operation lasted 3 h 30 min. The temperature was then allowed to return to room-temperature and the mixture allowed to stand for about 15 hours. Under reduced pressure and without going beyond 50° C., the pyridine was distilled off. After cooling, 3.5 l of water and 3.5 l of benzene were added.

The aqueous phase containing pyridine hydrochloride was decanted and again extracted with 3 l of benzene. The benzene fractions were collected and successively washed with a 36%-aqueous solution of hydrochloric acid to pH=1 and then with distilled water to neutrality. The benzene was eliminated by distillation under reduced pressure without going beyond 50° C. in the mass. The crude ester was then rectified by fractions each of 700 to 800 g and the fraction boiling between 130° C./0.5 mm Hg and 135° C./0.1 mm Hg was collected.

In this manner, 3.420 kg of a mixture of glyceryl, 1,2-and 1,3-bis-(di-n-propylacetates) were obtained. ("Mixture A").

Yield: 78%.

$n_D^{20} = 1.4461$.

Infra-red spectrum (film): OH large at 3490 cm⁻¹, CH₃, CH₂ at 2950 cm⁻¹ (S), 2880 cm⁻¹ (S), CO ester at 1730 cm⁻¹ (S), 1150 cm⁻¹ (S), and large.

The mixture so obtained contained:
about 90% of glyceryl 1,2- and 1,3-(di-n-propylacetates) i.e. about 70% of 1,3 diester and about 30% of 1,2-diester.
about 7% of glyceryl 1-(di-n-propylacetate)
about 2% of glyceryl tri-(di-n-propylacetate)
about 1% of impurities i.e. glycerol and di-n-propylacetic acid.

EXAMPLE 11

Preparation of a mixture of glyceryl 1,2- and 1,3-bis-(di-n-propylacetates)

Into a 2-l flask equipped with a reflux condenser were introduced 893 g (900 ml) of N,N-dimethylformamide, 77.4 g (0.6 mol) of 1,3-dichloro-2-propanol and 206.4 g (1.24 mol+3%) of sodium di-n-propylacetate. Under nitrogen atomsphere and vigorous stirring, the medium was brought to 100° C. and this temperature was maintained for 8 hours. The maximum amount of solvent was then distilled off under reduced pressure (≃20 mm Hg) and 893 g of a distillate was collected. To the residue so obtained (≃350 g) were then added 300 g of distilled water and 537 g (620 ml) of toluene. The organic phase was successively washed with 300 g of distilled water, a solution of 30 g of sodium carbonate in 400 g of distilled water and finally with as many fractions of 300 g of distilled water as required to obtain a neutral pH. After drying on sodium sulphate, the solvent was eliminated under reduced pressure with a rotary evaporator so that a crude mixture of final products (≃201 g; ≃97.3%) was obtained. This mixture was rectified under high vacuum and the fraction boiling at 152° C. under 0.2 mm Hg was collected.

In this manner, a mixture of glyceryl 1,2- and 1,3-bis-(di-n-propylacetates) ("Mixture B") was provided in the form of a colourless liquid.

$n_D^{20} = 1.4476$ $$\frac{\text{Glyceryl 1,3-bis-(di-n-propylacetate)}}{\text{Glyceryl 1,2-bis-(di-n-propylacetate)}} = 1.54$$

Glyceryl 1-(di-n-propylacetate): about 1%.

Glyceryl tri-(di-n-propylacetate): not detected (<0.5%).

1,3-Dichloro-2-propanol: 0.002%.

Following the same procedure as that described above, the following mixtures of diesters were prepared:

Mixture

Glyceryl 1,2-bis-(di-n-propylpropionate) and glyceryl 1,3-bis-(di-n-propylpropionate)
B.P.: 172°–180° C. under 0.4 mm Hg.
$n_D^{23} = 1.4567$.
Infra-red spectrum (film): OH at 3480 cm⁻¹ (m), C═O at 1740 cm⁻¹ (S), C—O at 1170 cm⁻¹ (m).

Glyceryl 1,2-bis-(di-n-propylmethoxyacetate) and glyceryl 1,3-bis-(di-n-propylmethoxyacetate).
$n_D^{14} = 1.4556$.
Infra-red spectrum (film): OH at 3480 cm⁻¹ (m), C═O at 1755 cm⁻¹ (S), COO at 1100–1200 cm⁻¹ (m).

Further operations for the preparation of a mixture of glyceryl 1,2-and 1,3- bis-(di-n-propylacetates) were carried out in accordance with the aforesaid process but respecting the following working conditions:

| Esterification T (°C.) | Time (h) | Excess in sodium di-n-propyl-acetate (in %) | Dimethylformamide Water | Yield (in %) |
|---|---|---|---|---|
| 110 | 9 | — | no water | 88.8 |
| 100 | 8 | 5(*) | no water | 93.9 |
| 100 | 5 | — | ≃95/5 | 90.7 |

-continued

| Esterification | | Excess in sodium | | |
|---|---|---|---|---|
| T (°C.) | Time (h) | di-n-propyl-acetate (in %) | Dimethylformamide Water | Yield (in %) |
| 100 | 7 | — | ≈95/5 | 94 |

(*)dimethylformamide used in amounts 5 times the total amount of the reagents.

EXAMPLE 12

Preparation of 1,2-propanediol bis-(di-n-propylacetate)

Into a perfectly dry flask were introduced 76.1 g (1 mol) of rectified 1,2-propanediol and 1600 g of anhydrous pyridine.

Under vigorous stirring, 338.3 g (2.08 mols) of di-n-propylacetyl chloride were added in 15 minutes. The reaction was found to be exothermic since the temperature of the medium increased from 22° C. to 61° C. The mass was then heated to 90° C. and maintained at this temperature for 8 hours. The pyridine in excess was eliminated under reduced pressure with a rotary evaporator (temperature in the mass $\leq 60°$ C.) and the dry extract was taken up in a mixture of 800 ml of 36%-hydrochloric acid aqueous solution diluted at 1/10° and 800 ml of ethyl ether. The acid phase (pH≈1) was decanted and the organic phase was successively washed with 800 ml of a 5-aqueous solution of sodium bicarbonate, 800 ml of a 15% -aqueous solution of sodium carbonate and two fractions each of 800 ml of distilled water. After drying on sodium sulphate the organic phase was filtered and the ether was eliminated under vacuum using a rotary evaporator. The residue (316.4 g-yield: 96.3%) was rectified and the innermost fraction was collected.

In this manner, 278.2 g of 1,2-propanediol bis-(di-n-propylacetate) were obtained in the form of a colourless liquid.

Yield: 84.7% from 1,2-propanediol.
B.P.: 115°-120° C. under 0.1-0.2 mm Hg.
Infra-red spectrum (film): $CH_3$, $CH_2$, CH at 2960-2880 cm$^{-1}$ (m), C═O at 1740 cm$^{-1}$ (S), C—O at about 1200 cm$^{-1}$ (m).

Using the same method as that described above, the compounds hereunder were prepared:

Compound 1,3-Propanediol bis-(di-n-propylacetate).
Yield: 80.5%.
B.P.: 117°-124° C. under 0.1-0.2 mm Hg.
Infra-red spectrum: $CH_3$, $CH_2$, CH at 2960-2880 cm$^{-1}$ (m), C═O at 1740 cm$^{-1}$ (S), C—O at about 1200 cm$^{-1}$ (m).

1,2-Propanediol bis-(1-methyl-cyclohexylcarboxylate).
Yield: 81.5%.
B.P.: 120°-130° C. under 0.4 mm Hg.
$n_D^{27} = 1.4643$.
Infra-red spectrum: $CH_3$, $CH_2$, CH at 3000-2800 cm$^{-1}$ (m) C═O at 1735 cm$^{-1}$ (S), COO at 1200-1140 cm$^{-1}$ (m).

1,3-Propanediol bis-(1-methyl-cyclohexylcarboxylate).
B.P.: 130°-140° C. under 0.25 mm Hg.
$n_D^{29} = 1.4666$.
Infra-red spectrum: $CH_3$, $CH_2$ at 3000-2800 cm$^{-1}$ (m), C═O at 1730 cm$^{-1}$ (S), COO at 1205-1130 cm$^{-1}$ (m).

EXAMPLE 13

Preparation of 1,3-butanediol bis-(di-n-propylacetate)

Into a perfectly clean and dry flask were introduced 90.1 g (1 mol) of rectified 1,3-butanediol and 1600 ml of anhydrous pyridine. Under vigorous stirring 338.3 g (2.08 mols) of di-n-propylacetyl chloride were progressively added in about 30 minutes. The reaction was found to be exothermic since the temperature of the medium increased from 30° C. to about 35° C. The mass was then heated to 90° C. and maintained at this temperature for 10 hours. The maximum amount of pyridine was then eliminated under reduced pressure (15-20 mm Hg) with a rotary evaporator, the residue was taken up in 800 ml of a 36%-hydrochloric acid aqueous solution and the mixture was extracted with three fractions each of 300 ml of ethyl ether. The ethereal phases were collected, washed with 800 ml of a saturated aqueous solution of sodium bicarbonate and then with 800 ml of a 15% by weight aqueous solution of potassium carbonate to eliminate the acid chloride in excess.

The ethereal phases were then washed to neutrality with as many fractions each of 800 ml of distilled water as required and then decanted to the maximum.

After drying on sodium sulphate, the ether was evaporated off with a rotary evaporator first under atmospheric pressure and then under vacuum and the residue was rectified.

In this manner, 1,3-butanediol bis-(di-n-propylacetate) was obtained in the form of a colourless limpid liquid.

Yield: 86.4%.
B.P.: 120°-125° C. under 0.15 mm Hg.
$n_D^{23} = 1.4372$.
Infra-red spectrum (film): C═O at 1735 cm$^{-1}$ (S), C—O at 1100-1200 cm$^{-1}$ (S).

Using the same procedure as that described above the following compounds were prepared:

Compounds 1,2-Propanediol bis-(di-n-propylacetate).
Yield: 92%.
B.P.: 124° C. under 0.5 mm Hg.
1,3-Propanediol bis-(di-n-propylacetate).
Yield: 93.5%.
B.P.: 121°-127° C. under 0.4 mm Hg.
1,4-Butanediol bis-(di-n-propylacetate).
Yield: 87.5%.
B.P.: 140° C. under 0.3 mm Hg
$n_D^{18} = 1.4410$
Infra-red spectrum (film): $CH_3$, $CH_2$,CH at 2960-2940-2880 cm$^{-1}$ (m), C═O at 1735 cm$^{-1}$ (S), COO at 1170 cm$^{-1}$ (m).

Diethyleneglycol bis-(di-n-propylacetate)
Yield: 78.5%
B.P.: 148°-152° C. under 0.3 mm Hg
$n_D^{23} = 1.4395$
Infra-red spectrum (film): C═O at 1735 cm$^{-1}$ (S), C—O at 1100-1200 cm$^{-1}$ (S).

Thiodiglycol bis-(di-n-propylacetate).
Yield: 80.5%.
B.P.: 164°-168° C. under 0.4 mm Hg.
$n_D^{23} = 1.4603$.
Infra-red spectrum (film): $CH_3$, $CH_2$, CH at 3000-2800 cm$^{-1}$ (m), C═O at 1735 cm$^{-1}$ (S), COO at 1160-1140 cm$^{-1}$ (m).

1,2-Cyclohexanediol bis-(di-n-propylacetate) (mixture of cis and trans isomers)

Yield: 86.1%
B.P.: 140°-150° C. under 0.01 mm Hg
$n_D^{18} = 1.4543$
Infra-red spectrum (film): C=O at 1740 cm$^{-1}$ (S), COO at 1100-1200 cm$^{-1}$ (m).

EXAMPLE 14

Preparation of 2-butyn-1,4-diol bis-(di-n-propylacetate)

Into a perfectly clean and dry flask were introduced 86 g (1 mol) of rectified 2-butyn-1,4-diol and 1600 ml of anhydrous pyridine. While stirring, the inner temperature was brought to 0 to +5° C. by means of a refrigerating bath and then 338.3 g (2.08 mols) of distilled di-n-propylacetyl chloride were progressively introduced while maintaining the temperature below +15° C. This operation lasted about 75 to 90 minutes. The reaction medium was then allowed to return to room-temperature and maintained for 48 hours under stirring.

The subsequent operations of purification were identical to those carried out in the foregoing Example 13.

In this manner 2-butyn-1,4-diol bis-(di-n-propylacetate) was obtained in the form of a colourless limpid liquid.

Yield: 81.4%.
B.P.: 145±5° C. under 0.4 mm Hg.
$n_D^{18} = 1.4528$.
Infra-red spectrum (film): CH$_3$, CH$_2$, CH at 2950-2880 cm$^{-1}$ (m), C=O at 1740 cm$^{-1}$ (S), COO at 1150 cm$^{-1}$ (S).

Using the procedure hereabove described, the compound hereunder was prepared from 2-buten-1,4-diol (cis isomer).

Compound

2-Buten-1,4-diol bis-(di-n-propylacetate) (cis isomer).
Yield: 91.6%.
B.P.: 123° C. under 0.15 mm Hg or 140° C. under 0.25 mm Hg.
$n_D^{20} = 1.4496$.
Infra-red spectrum (film): CH at 3050 cm$^{-1}$ (m), CH$_3$, CH$_2$ at 2970 cm$^{-1}$ (S), 2950 cm$^{-1}$ (S), CO 1740 cm$^{-1}$ (S), ester 1175 cm$^{-1}$ (S).

EXAMPLE 15

Preparation of 1,2,4-butanetriol tri-(di-n-propylacetate)

Into a perfectly clean and dry flask were introduced 106.1 g (1 mol) of rectified 1,2,4-butanetriol and 1600 ml of anhydrous pyridine. While stirring, 507.4 g (3.12 mols) of di-n-propylacetyl chloride were added in 60 to 90 minutes care being taken to maintain the temperature below 30° C. The reaction medium was then stirred at room-temperature for 72 hours. The subsequent operations of purification were identical to those carried out in the foregoing Example 13.

In this manner, 1,2,4-butanetriol tri-(di-n-propylacetate) was obtained in the form of a limpid liquid.

Yield: 80.1%.
B.P.: 180° C. under 0.009 mm Hg or 190° C. under 0.02 mm Hg.
$n_D^{15} = 1.4492$.
Infra-red spectrum (film): C=O at 1740 cm$^{-1}$ (S), COO at 1170 cm$^{-1}$ (S).

Following the same procedure as that described above, the compounds hereunder were prepared:

Compounds

Trimethylolpropane tri-(di-n-propylacetate)
Yield: 77.5%.
B.P.: 190°-191° C. under 0.2 mm Hg.
$n_D^{27} = 1.4462$.
Infra-red spectrum (film): CH$_3$, CH$_2$, CH at 3000-2800 cm$^{-1}$ (m), C=O at 1740 cm$^{-1}$ (S), COO at 1200-1100 cm$^{-1}$ (m).

Pentaerythritol tetra-(di-n-propylacetate).
Yield: 78%.
M.P.: 56° C. (methanol).
Infra-red spectrum: CH$_3$, CH$_2$ at 2965 cm$^{-1}$ (m), 2940 cm$^{-1}$ (m), 2880 cm$^{-1}$ (m), CO ester at 1735 cm$^{-1}$ (S), 1170 cm$^{-1}$ (m).

EXAMPLE 16

Preparation of N-(di-n-propylacetyl)-diethanolamine bis-(di-n-propylacetate)

Into a perfectly clean and dry flask were introduced 105.1 g (1 mol) of rectified diethanolamine and 1600 ml of anhydrous pyridine. While stirring, 507.4 g (3.12 mols) of di-n-propylacetyl chloride were added in 30 to 45 minutes, care being taken to maintain the temperature below +30° C. The reaction medium was then stirred at room-temperature for 48 hours.

The subsequent operations of purification were identical to those carried out in the foregoing Example 13.

In this manner, N-(di-n-propylacetyl)-diethylanolamine bis-(di-n-propylacetate) was obtained in the form of a yellow limpid liquid.

Yield: 67%.
B.P.: 190° C. under 0.06 mm Hg.
$n_D^{18} = 1.4589$.
Infra-red spectrum (film): O—C=O at 1740 cm$^{-1}$ (S), N—C=O at 1650 cm$^{-1}$ (m), COO at 1100-1200 cm$^{-1}$ (m).

EXAMPLE 17

In accordance with known pharmaceutical techniques, a soft-gelatin capsule, containing the following ingredients, was prepared:

| Ingredient | mg |
| --- | --- |
| Mixture of glyceryl 1,2- and 1,3-bis-(di-n-propylacetates) ("Mixture B") | 500 |
| Gelatin | 212 |
| Glycerol | 83 |
| Ethyl p-hydroxybenzoate (sodium salt) | 4 |
| Propyl p-hydroxybenzoate (sodium salt) | 2 |
| Titane dioxide | 4.4 |

We claim:

1. A pharmaceutical or veterinary composition for treating anoxia, convulsive states and seizures, which comprises as essential active ingredient at least one glyceryl ester selected from the group consisting of glyceryl 1,2-bis-(di-n-propylacetate) and glyceryl 1,3-bis-(di-n-propylacetate), in combination with a pharmaceutical carrier or excipient therefor, in dosage unit form containing 50 to 600 mg. of active ingredient.

2. A pharmaceutical or veterinary composition, as defined by claim 1, which comprises as essential active ingredient a mixture of glyceryl 1,3-bis-(di-n-propylacetate) and 1,2-bis-(di-n-propylacetate) in a ratio from about 1.43:1 to about 1.54:1.

3. A method of treating anoxia, convulsive states and seizures in a human being in need of such treatment, which comprises administering to said human being an effective dose of from 10 mg/kg to 50 mg/kg of a glyceryl ester selected from the group consisting of glyceryl 1,2-bis-(di-n-propylacetate) and glyceryl 1,3-bis-(di-n-propylacetate).

4. The method of claim 3 wherein the glyceryl ester is a mixture of glyceryl 1,3-bis-(di-n-propylacetate) and glyceryl 1,2-bis-(di-n-propylacetate).

5. The method of claim 4 wherein the glyceryl ester is a mixture of glyceryl 1,3-bis-(di-n-propylacetate) and 1,2-bis-(di-n-propylacetate) in a ratio from about 1.43:1 to about 1.54:1.

6. The method of claim 3 wherein the anticonvulsant action is antiepileptic.

* * * * *

Notice of Adverse Decision in Interference

In Interference No. 101,397, involving Patent No. 4,423,071, M. Chignac, C. Grain, F. Jammot, C. Pigerol, P. Eymard and B. Ferrandes, POLYOL DERIVATIVES, PROCESSES FOR PREPARING THE SAME AND THEIR USES IN THERAPEUTICS, final judgment adverse to the patentees was rendered July 1, 1986, as to claims 1-6.

[*Official Gazette September 16, 1986.*]